(12) United States Patent
Zhou et al.

(10) Patent No.: US 6,309,608 B1
(45) Date of Patent: Oct. 30, 2001

(54) METHOD AND APPARATUS FOR ORGANIC SYNTHESIS

(75) Inventors: Peng Zhou, Westborough, MA (US); Stephen Matson, 15 Withington La., Harvard, MA (US) 01451

(73) Assignee: Stephen Matson, Harvard, MA (US)

( * ) Notice: Subject to any disclaimer, the term of this patent is extended or adjusted under 35 U.S.C. 154(b) by 0 days.

(21) Appl. No.: 09/298,743

(22) Filed: Apr. 23, 1999

Related U.S. Application Data

(60) Provisional application No. 60/082,841, filed on Apr. 23, 1998.

(51) Int. Cl.[7] .................................................. B01L 11/00
(52) U.S. Cl. .......................... 422/131; 422/101; 422/102; 422/103; 422/104; 422/134; 435/287.2; 435/288.3; 435/288.5; 435/305.3; 436/178; 210/321.75; 210/348
(58) Field of Search .................................. 422/131, 134, 422/101, 102, 103, 104; 435/288.3, 288.5, 287.2; 436/178; 210/321.75

(56) References Cited

U.S. PATENT DOCUMENTS

| | | | |
|---|---|---|---|
| 5,108,704 | * | 4/1992 | Bowers et al. .......................... 422/70 |
| 5,137,698 | * | 8/1992 | Ansorge et al. ....................... 422/242 |
| 5,141,719 | * | 8/1992 | Fernwood et al. .................... 422/101 |
| 5,529,756 | * | 6/1996 | Brennan ................................ 422/131 |
| 5,538,694 | * | 7/1996 | Delius ................................... 422/131 |
| 5,716,584 | * | 2/1998 | Baker et al. .......................... 422/131 |
| 5,736,105 | * | 4/1998 | Astle .................................... 422/100 |
| 5,762,881 | * | 6/1998 | Harness et al. ....................... 422/132 |
| 5,961,925 | * | 10/1999 | Ruediger et al. ....................... 422/99 |
| 6,054,100 | * | 4/2000 | Stanchfield et al. ................. 422/102 |
| 6,126,904 | * | 10/2000 | Zuellig et al. ....................... 422/130 |
| 6,149,869 | * | 11/2000 | Antonenko et al. ................... 422/99 |
| 6,159,368 | * | 12/2000 | Moring et al. .................. 210/321.75 |

\* cited by examiner

*Primary Examiner*—Jill Warden
*Assistant Examiner*—Kathryn Bex
(74) *Attorney, Agent, or Firm*—Bruce F. Jacobs

(57) ABSTRACT

Methods and apparatus for the semi-automated synthesis of libraries of organic compounds are disclosed. More specifically, the present invention comprises multi-vessel reaction blocks, accessory components, and complementary workstations designed to facilitate the semi-automated production of libraries of chemical compounds by combinatorial and parallel synthesis techniques. The invention is particularly well suited to the conduct of solid-phase or solution-phase parallel syntheses of single compounds and compound mixtures in a high-throughput manner.

22 Claims, 18 Drawing Sheets

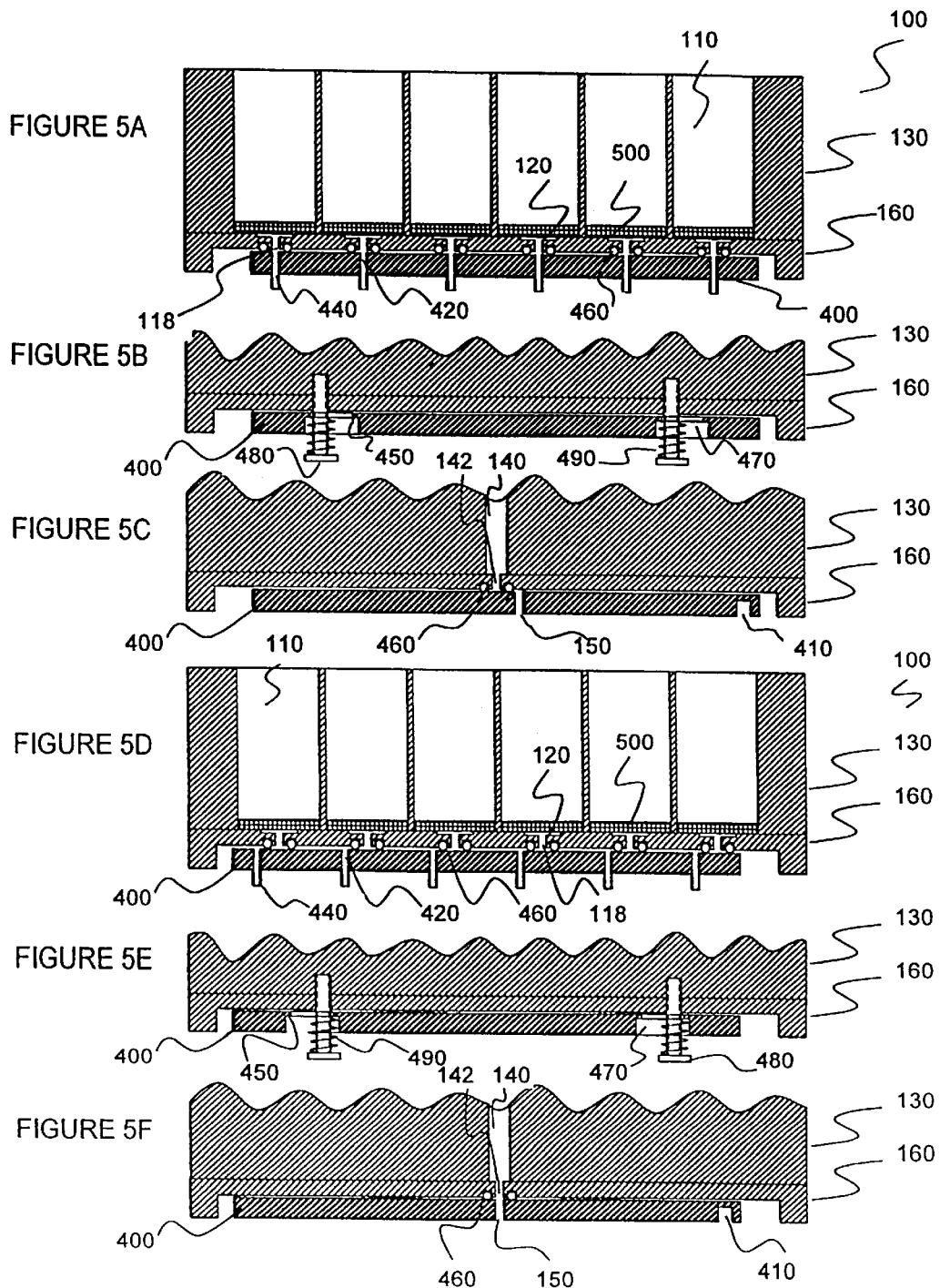

METHOD AND APPARATUS FOR ORGANIC SYNTHESIS

This application claims benefit of Prov. No. 60/082,841 filed Apr. 23, 1998.

FIELD OF THE INVENTION

The present invention relates generally to methods and apparatus for generating chemical libraries of organic compounds. More specifically, the invention relates to methods and apparatus for improving the productivity of chemists—in particular, of "combinatorial chemists" involved in drug discovery—by permitting them to conduct large numbers of reactions simultaneously and to perform the associated physical and chemical steps involved in separation and compound recovery (e.g., resin washing and compound transfer, respectively) in an efficient manner that is amenable to various degrees of automation. More particularly, the present invention relates to novel multi-vessel reaction blocks, wash plates, transfer boxes, and associated equipment with which high-throughput chemistry can be conducted.

BACKGROUND OF THE INVENTION

Historically the discovery and optimization of candidate compounds for development as drugs has been extraordinarily expensive and time-consuming. Although the relatively new approach of "rational drug design" has promise for the future, the pharmaceutical industry has generally relied on mass screening of many-membered "libraries" of chemical compounds for the identification of "lead" compounds worthy of further study and structure-activity relationship (SAR) work. To meet this need high-throughput screening (HTS) technology has been developed that permits pharmaceutical companies to evaluate hundreds of thousands of individual chemical entities per year. Typically, these screens involve measuring some interaction (e.g., binding) between a biological target such as an enzyme or receptor and chemical compounds under test. The screens generally commence with the addition of individual compounds (or mixtures of compounds) to the individual wells in a 96 or higher-well "microtiter" plate that contains the biological target of interest (e.g., a receptor, enzyme or other protein). Ligand/receptor binding or other interaction events are then deduced by, for instance, various spectrophotometric techniques. Those chemical entities that exhibit promise in initial screens (e.g., that bind a biological target with some threshhold affinity) are then subjected to chemical optimization, SAR work, other types of testing, and, if warranted, eventual development as drugs.

Now that HTS has simplified and made more cost-effective the task of determining whether large chemical libraries contain promising lead compounds or "hits", many pharmaceutical companies are limited not by their ability to screen candidate compounds but rather by their ability to synthesize them in the first place. At one point, most pharmaceutical companies relied on their historical collections of natural products and individually synthesized chemical entities as compound libraries to be subjected to mass screening. However, expanding these libraries—especially with a view toward increasing the "diversity" of the chemical space that they probe—has proven problematic. For instance, the cost of having a synthetic organic or medicinal chemist synthesize individual molecules in a serial fashion has been estimated to be several thousand dollars, and this is obviously a painstakingly slow process.

Thus, the advent of high-throughput screening has created a need for correspondingly high-throughput chemical synthesis (HTCS) to feed this activity. "Combinatorial chemistry" and related techniques for high-throughput parallel syntheses of large chemical libraries were created in response to this need (Gallop, M. A. et al, "Applications of Combinatorial Technologies to Drug Discovery: 1. Background and Peptide Combinatorial Libraries," *J. Med. Chem.*, 37 (9) :1233–1251 (1994); Gordon, E. M. et al, "Applications of Combinatorial Technologies to Drug Discovery: 2. Combinatorial Organic Synthesis, Library Screening Strategies, and Future Directions," *J. Med. Chem.*, 37 (10):1385–1401 (1994); Baum, R. M., "Combinatorial Approaches Provide Fresh Leads for Medicinal Chemistry," *C&E News*, pp. 20–26, Feb. 7, 1994; Plunkett, M. J. et al, "Combinatorial Chemistry and New Drugs," *Scientific American*, 276 (4):68–73 (1997); Borman, S., "Combinatorial Chemistry," *C&E News*, pp. 44–67, Apr. 6, 1998). To simplify the separation of intermediate compounds during multistep organic syntheses, much of this chemistry is generally performed while the compound being synthesized is covalently immobilized on small support beads. Once the chemical building blocks have been properly assembled, the desired compounds are usually cleaved from their supports (often highly swellable polymeric resins) before being carried through to HTS.

Various definitions of "combinatorial chemistry" and "combinatorial synthesis" have been proposed and are in current use. Some synthesis strategies (e.g., "split-and-mix") are truly "combinatorial" in nature and have as their hallmark the ability to produce very large libraries; indeed, as many as a million library members can be synthesized in a modest number of reactions (and correspondingly small number of reaction vessels) by virtue of the exponential mathematics involved. One of the several limitations of such approaches, however, is the difficulty of identifying the particular individual chemical species responsible for any activity measured in an assay of what is generally a mixture of compounds.

Other approaches such as high-throughput parallel synthesis are typically used to produce somewhat smaller chemical libraries containing, for example, from several hundred to several hundred thousand individual compounds. Here, discrete compounds (and occasionally mixtures) are spatially segregated during chemical synthesis so no ambiguity exists as to the identity of any compound producing a "hit." However, parallel synthesis requires that chemical reactions be conducted in parallel in a relatively large number of reaction vessels, thus placing a premium on the ability to automate and improve the speed and efficiency of the synthetic process.

The terms "combinatorial chemistry," "combinatorial synthesis," and "parallel synthesis" are used herein synonymously and interchangeably to denote various high-throughput approaches for the preparation of chemical libraries, whether by solid-phase or solution-phase synthesis. Although the present invention is described primarily in terms of its capabilities for solid-phase synthesis, the invention is not so limited. Similarly, the present description focuses principally on the parallel synthesis of discrete compounds (i.e., one chemical entity per reaction chamber or vessel), although truly combinatorial, split-and-mix synthesis as well as the synthesis of compound mixtures can be performed equally well with the apparatus and method of the present invention.

There currently exist several different approaches for the parallel, solid-phase synthesis of discrete compounds, with somewhat different types of apparatus being best suited to each approach. The approaches described here can be referred to as "spatially addressable" strategies for the reason that, generally, each unique compound is synthesized (and addressable) at a separate point in space—that is, one compound is synthesized per reaction vessel in a multi-vessel "reaction block". The devices and equipment used to execute these different spatially addressable synthesis strategies differ considerably in terms of their degree of sophistocation, automation, and cost—ranging from fully automated robotic synthesizers presently costing as much as several hundred thousand dollars to simple, disposable, inexpensive 96-well microtiter plates modified for chemical synthesis.

Most high-throughput chemical syntheses (HTCS) performed in the context of combinatorial chemistry and parallel synthesis are presently conducted in multi-vessel reaction assemblies often referred to as "reaction blocks" by virtue of their monolithic construction. In most solid-phase syntheses, the compound being constructed is covalently attached to resin beads and so many of these multi-vessel reaction blocks include provision for a porous frit to retain the polymer resin beads (and compounds attached thereto) in the reaction vessel during the multiple resin washing steps that are used to remove excess reagents (e.g., building blocks, solvents, catalysts, etc.) after individual reaction steps. In some designs the compounds being synthesized are immobilized on porous/solvent-swollen "pins" that extend into individual reaction chambers (Geysen, H M et al, *Proc.Natl.Acad.Sci.USA*, 81:3998 (1984); U.S. Pat. No. 4,708,871 (1987)). Other approaches utilize small porous sacks or "teabags" to contain the resin (Houghten, R A, *Proc. Natl.Acad.Sci.USA,* 82:5131 (1985)).

Since most chemical libraries synthesized by HTCS are destined for mass screening, and since the 96-well plate is the standard platform for assay of biological activity by HTS, most reaction vessel asssemblies or reaction blocks for combinatorial synthesis contain either 96 vessels or a simple fraction of that number (e.g. 48 or 24). One of the first automated instruments specifically designed and marketed with combinatorial chemistry in mind is the Model 396 MPS ("multiple peptide synthesizer", a name reflective of the original market for the instrument) manufactured by Advanced ChemTech, Inc. (Louisville, Ky.). Subsequent to the introduction of the Model 396, the Advanced ChemTech product line was expanded to include other instruments, e.g. the Model 496. In both of the instruments, syntheses are conducted in a plastic (Teflon®) reaction block in which 96 discrete reaction chambers or vessels have been machined. One or more of these reaction blocks is placed within the working space of an automated liquid handling system or "robot" capable of delivering various solvents and reagents to discrete reaction vessels. A frit at the base of each reaction vessel retains resin (and compound) during resin washing steps, with fluids being removed from the reaction chambers through a siphon arrangement. The siphon system inherently limits usefulness of the device in terms of the pressures at which it can successfully be operated—and, in particular, the maximum pressure differences that can be tolerated before the contents of the reaction vessels leak out.

Since the Advanced ChemTech automated synthesizers and reaction blocks were among the first to market, they have been used extensively in combinatorial chemistry laboratories. However, the 96-vessel reaction blocks have a number of drawbacks. Due to their monolithic, machined construction, they are expensive to manufacture and damage to any part of a block can cause the entire block to be unusable. Moreover, because they are machined from plastic materials (to provide inert and solvent-resistant vessel surfaces in contact with the chemistries being conducted within them), the blocks have poor thermal conductivity. Thus heating or cooling to reaction conditions can be slow. Another limitation of these reaction blocks is a difficulty of achieving gas and vapor-tight seals, especially where aggressive and/or volatile solvents and elevated reaction temperatures are utilized.

Finally, the Model 396 and 496 reaction blocks are physically large and heavy. Their size and weight interfere with their placement on and removal from the platforms of the robotic workstations used to address them. It is often desirable to be able to move the reaction blocks, e.g. to permit reactions to be conducted off-line thereby freeing up expensive workstation space, but the cumbersome nature of the Model 396 and 496 reaction blocks makes this inconvenient. Just as significant a drawback, however, is that, despite containing 96 reaction vessels (and compounds or mixtures thereof), it is impossible to cleave these compounds directly into the wells of the much smaller (3⅜"×5") 96-well microtiter plates most commonly used for compound storage and assay. The footprint of the Model 396 and 496 reaction blocks is incompatible with the footprint of conventional microtiter plates, which makes it impossible to address these reaction blocks with other automated equipment which has been designed around the standardized platform of the 96-well plate. Also, there is no convenient way of "reformatting" or transferring compounds to such microplates if they are initially cleaved into test tubes or vials.

Advanced ChemTech manufactures still other reaction blocks and automated synthesizers including a Model 440 system based on a reaction block containing 40 8-mL reaction vessels, as well as lower-end semi-automated and manual systems marketed as their ReacTech and LabTech product lines. These related products suffer from many of the same disadvantages and limitations discussed above.

Another reaction block design is described in U.S. Pat. No. 5,609,826, of Ontogen Corp. Ontogen's "OntoBLOCK" reaction block system is comprised of two similar "alpha" and "beta" blocks, each of which holds 48 2-mL reaction chambers; a pair of two blocks can deliver cleaved compounds directly into 96-well plates. Individual reaction chambers, each fitted with porous bottom frits, are polymeric and removable; in use, they slip into an anodized aluminum block that serves to hold the reaction chambers in place and have S-shaped trap tubes for draining vessel contents. The reaction blocks can be closed with elastomeric seals to maintain an inert atmosphere and/or to contain volatile solvents at elevated reaction temperatures. The Ontogen reaction blocks are fitted with metal pins to facilitate securing the blocks on complementary docking stations. The pins also permit the blocks to be moved and addressed by robotic handling equipment. The S-trap tube inherently limits usefulness of the device in terms of the maximum pressure difference that can be tolerated before the contents of the reaction vessels leak out.

A somewhat different type of highly automated instrument for HTCS—again, with origins in solid-phase peptide synthesis—is exemplified by the Nautilus™ 2400 organic synthesizer manufactured by Argonaut Technologies, Inc. (San Carlos, Calif.). This instrument is not based on a reaction block per se. Rather it directs reagents through an assembly of valves to 24 individual glass reaction vessels mounted on the synthesizer. Like the Advanced ChemTech synthesizer, the Nautilus 2400 instrument is expensive and although capable of performing a wide range of chemistries is limited in terms of the number of syntheses that can be conducted simultaneously. Argonaut's Quest™ 210 manual synthesizer is similar in concept and is designed to perform but 20 reactions in parallel.

Several other reaction block designs and automated systems based upon them combine some of the above-cited features and are regarded as "hybrids" in certain respects. For example, (i) the CombiTec synthesizer developed by Tecan (Research Triangle Park, N.C.) and marketed by Perkin-Elmer (Foster City, Calif.), (ii) the Pathogenesis/RAM™ synthesizer developed and marketed by Bohdan Automation, Inc. (Mundelein, Ill.), and (iii) the Combi-Syn™ synthesizer under development by CombiChem, Inc. (San Diego, Calif.) all rely on glass reaction vessels fitted to and/or within a manifold with provisions for fluid supply and withdrawal. Although addressable by liquid handling robots, the CombiSyn™ synthesizer relies on an arrangement of fluid valves (as in Argonaut's Nautilus™ product) to supply and remove reagents and solvents from the reaction vessels. All rely on porous frits to retain resin within individual reaction vessels.

At the other extreme from these expensive fully automated synthesizers there exists several simpler and less expensive products marketed for combinatorial synthesis that are based largely on modifications to the standard 96-well microtiter plate. For example, Polyfiltronics/Whatman (Rockland, Mass.) and Millipore (Bedford, Mass.) both market solvent-resistant 96-well plates fitted with solvent-resistant filters for resin/solution retention. Although synthetic versatility is limited—they cannot readily be sealed—they are inexpensive to manufacture and thus are disposable. However, they are unsuited for performing multistep chemical reactions, especially at elevated temperature and/or with volatile solvents.

Other "low-end" product offerings include the MultiReactor™ available from RoboSynthon, Inc. (Burlingame, Calif.) and the Multiblock available from CSPS (Tucson, Ariz.). However, the former product is limited to solution-phase chemistries, while the latter is based on the use of an unwieldy array of plastic syringes pressed into service as chemical reactors. The SPS (Solid Phase Synthesis) Reactor offered by J-Kem Scientific, Inc. (St. Louis, Mo.) is similar in that it relies upon an array of syringe barrels fitted with porous plastic frits for resin retention.

Several other reaction blocks designed specifically for combinatorial/parallel synthesis fall between the extremes represented by "high-end", fully automated organic synthesizers on the one hand and "low-end" reaction assemblies based on plastic microtiter plates and syringe arrays on the other hand. Typical of these products are the FlexChem™ reaction block system developed by Robbins Scientific Corp. (Sunnyvale, Calif.) and the Calypso System™ offered by Charybdis Technologies, Inc. (Carlsbad, Calif.).

The Robbins Scientific FlexChem™ synthesis/filtration block has a single molded polypropylene unit that contains 96 2-mL reaction wells with porous polyethylene frits (for resin retention) pressed into the bottom of each chamber. The one-piece plastic block can be sealed top and bottom against elastomeric septa or gaskets by clamping it tightly between two metal sealing covers—the top one of which is provided with beveled holes to permit access to individual reaction wells via a septum-piercing needle of a robotic liquid handler. The synthesis/filtration block has the same footprint as a standard 96-well microtiter plate so that cleaved compounds can be transferred directly to same. A vacuum manifold fits the bottom of the reaction block and permits withdrawal of excess reagents and reaction and wash solvents from the reaction wells inbetween reaction steps. A second, larger vacuum manifold permits recovery of cleaved compounds into 96-well plates housed therein. The Robbins Scientific reaction block can also be used in conjunction with a rotating incubator (for resin agitation and heating during reaction steps) and a 96-channel dispenser (for addition of wash solvent after reaction steps).

A major disadvantage of Robbins Scientifics' FlexChem™ synthesis/filtration block is that it requires considerable manual intervention on the part of the combinatorial chemist—especially in the time-consuming and laborious steps of resin washing. Thus, operations can at best be semi-automated. Additionally, the FlexChe™ reactor blocks are constructed from a polypropylene material which has poor thermal conductivity and reportedly contains high levels of extractables. Also, it is difficult to seal the plastic block tightly and reliably against its top and bottom metal cover plates—the eight spring clamps and collar arrangement are unwieldy and inconvenient to use. Finally, the molded plastic reaction blocks—while much less expensive than some—are still expensive enough to invite reuse and so are not truly disposable. Over time, especially with repeated exposure to solvents, the polypropylene blocks tend either to become brittle and break—or to soften and lose mechanical rigidity.

The Calypso System™ of Charybdis Technologies, Inc., is based on reusable, machined PTFE Teflon® blocks that contain 96 2-mL reaction vessels or "wells" spaced as per the standard microtiter plate format. (Other higher-capacity blocks are available that contain either 48 5-mL wells or 24 10-mL wells.) Separate reaction blocks are required for solid-phase and solution-phase syntheses. The reaction blocks come either with bottom filtration means for solid-phase syntheses or with closed bottoms for solution-phase chemistries. Like the Robbins Scientific product, Charybdis' block is sealed top and bottom against rubber septa (to internal pressures as high as 30 psi) by clamping it between metal plates with the aid of bolts. Again, the top metal plate is perforated to permit accessing individual reaction chambers via the needle of a robotic liquid handling system. Provisions for inerting the block (e.g., with nitrogen) are also made.

As with Robbins Scientifics' FlexChem™ synthesis/filtration block, a major drawback of the Charybdis Calypso System™ is the need for operator intervention during time-consuming resin washing operations; i.e., removal of wash solvents from the block is a manual operation. Also, the Calypso System™, while less expensive than the fully automated synthesizers reviewed above, is significantly more expensive than many of the "low-end" reaction blocks based on modified 96-well microtiter plates.

Accordingly, there exists a need in the art for a modestly priced yet versatile reaction block with which to conduct combinatorial chemistry and high-throughput parallel syntheses. Ideally, the reaction block should present only chemically inert surfaces to the reactant solutions so that compounds submitted for HTS are free of contaminants and extractables; the materials of which the block is constructed must resist aggressive solvents and severe reaction conditions (e.g., elevated temperatures); and the block should be constructed of a high-thermal-conductivity material to facilitate rapid and uniform heat transfer. Individual reaction vessels in the reaction block need to have fluid capacity of about 2 mL or greater and preferably can be fitted with porous plastic frits for resin retention. Means for retaining or removing the liquid contents of individual reaction vessels should be positive, reliable, and convenient. The reaction block must also be purgable with, e.g., inert gases.

There also remains a need in the art for reaction blocks and compound transfer tools with footprints corresponding to that of the standard 96-well microtiter plate. Moreover, the design of these components should facilitate transfer or reformatting of the contents of individual reaction vessels to the corresponding wells in the microtiter plates. Those prior-art reaction blocks which do feature the size and layout of microtiter plates suffer from one or more other serious drawbacks that prevent them from being regarded as appropriate solutions to the above-mentioned unsolved problems.

Finally, there remains a need in the art for relatively low-cost reaction blocks, wash plates, and associated wash stations and other workstations that minimize requirements for operator intervention during the most time-consuming steps in combinatorial/parallel synthesis, especially those steps associated with resin washing.

The present invention fulfills these and other heretofore unmet needs and provides cost-effective productivity tools for use in the construction of compound libraries useful in drug discovery.

SUMMARY OF THE INVENTION

The present invention provides novel multi-vessel (e.g., 48-vessel) reaction blocks, accessory components, e.g., for washing and compound transfer or purification, and complementary wash stations and other workstations designed to facilitate the semi-automated production of libraries of chemical compounds by combinatorial and parallel synthesis techniques. The invention is particularly well suited to the conduct of parallel synthesis of single compounds and compound mixtures in a high-throughput manner. The reaction block system of this invention is useful for conducting both solid-phase and solution-phase syntheses.

More particularly, the apparatus for use in synthesising a library of organic compounds includes:

(a) a reaction block assembly containing (i) multiple individual reaction vessels, each of the vessels having an open top, and a bottom surface with a drain hole located therein; (ii) a sealing means for simultaneously sealing the drain holes of each of the reaction vessels, said sealing means having a plurality of through-holes spatially corresponding to the drain holes of the reaction vessels and movable into and out of fluid communication with said drain holes;

(b) a washing plate assembly having a means for attachment to the reaction block; a recessed wash plate cavity in fluid communication with a fluid exit port; and a means for simultaneously controlling the drainage of all of the reaction vessels; and (c) a transfer assembly comprising a transfer box having an internal cavity sized to fit a receiving container, a transfer assembly cover plate shaped to mate with the reaction block assembly, and a means for accurately locating the transfer assembly cover plate on the transfer box.

The invention is further directed to a reaction block assembly for use in synthesising a library of organic compounds including:

(i) a reaction block having multiple individual reaction vessels, each of said vessels having an open top and a bottom surface with a drain hole located therein; and (ii) a sealing means for simultaneously sealing the drain holes of each of the reaction vessels in the reaction block, the sealing means having a plurality of through-holes which (a) spatially correspond to the drain holes of the reaction vessels and (b) are movable into and out of fluid communication with said drain holes.

The invention is further directed to a reaction block assembly for use in synthesising a library of organic compounds including:

(i) a reaction block having multiple individual reaction vessels, each of said vessels having an open top, and a bottom surface with a drain hole located therein; and (ii) a pressure-equalization means to prevent buildup of a pressure difference across the reaction vessels.

The invention is also directed to a washing plate assembly for use with a reaction block used to prepare a library of organic compounds which reaction block has multiple reaction vessels each having a separate drain hole. The washing plate assembly includes: a means for attachment of a wash plate to a reaction block; a recessed wash plate cavity in fluid communication with a fluid exit port; a means for opening or closing the drain holes of the reaction vessels; and a means for simultaneously controlling the drainage of all of the reaction vessels.

The invention is also directed to a transfer assembly for use with a reaction block used to prepare a library of organic compounds and having multiple reaction vessels each having a separate drain hole. The transfer assembly includes: a transfer box having an internal cavity sized to fit a receiving container, a cover plate which is shaped to mate with the reaction block assembly and has a plurality of holes spatially corresponding to the drain holes of the reaction vessels of the reaction block, a means for attachment of the reaction block to the cover plate; and a means for accurately locating the cover plate on the transfer box.

Specific novel features of the reaction block design include: (i) the reaction vessels bottom closure seal means, preferably a sliding seal plate with a plurality of O-ring seals around the drain hole of each reaction vessels that effectively and simply closes off the drain channels from each of the reaction vessels in the block assembly when desired; (ii) a pressure-equalization and reaction block purge means that prevents the buildup of undesirable pressure differences across the reaction vessels during reaction steps; (iii) means for sealing the interior of the reaction block, (iv) common valving means for controlling the drainage of each of the reaction vessels as a group, the valving means being located on a so-called "washing plate" or box that is separate and distinct from the reaction block assembly itself; and (v) fluid redirection/reformatting means. Preferably the sliding seal plate is spring-loaded and also serves as a means for relieving excess reaction vessel pressures when required.

BRIEF DESCRIPTION OF THE DRAWINGS

FIGS. 5A, 5B, 5C, 5D, 5E, and 5F are cross-sectional views of the reaction block and sliding seal plate according to a preferred embodiment. FIGS. 5A and 5D are sections taken at a plane passing through the reaction vessels of the reaction block; FIGS. 5B and 5E are sections taken at a plane passing through the reaction block locator pins; and FIGS. 5C and 5F are sections taken at a plane passing through the reaction block and sliding seal plate pressure-equalization/ purge holes.

FIG. 15A shows a top view of this plate; FIG. 15B is a magnified top view of a particular director channel in the top surface of this reformatting plate; and FIG. 15C shows a cross-sectional view along plane "A"—"A" of aforesaid director channel.

FIG. 16A illustrates the spatial orientation of the components when placed in the "vessel-open" configuration and readied for compound transfer, whereas FIG. 16B illustrates the spatial orientation of the components when in the "vessel-closed" configuration.

FIG. 17A illustrates the placement of a microtiter plate readied to accept cleaved compounds in columns numbered "1" through "6", whereas FIG. 17B illustrates plate placement when cleaved compounds are to be transferred into columns "7" through "12".

DETAILED DESCRIPTION OF THE INVENTION

Figure 1:
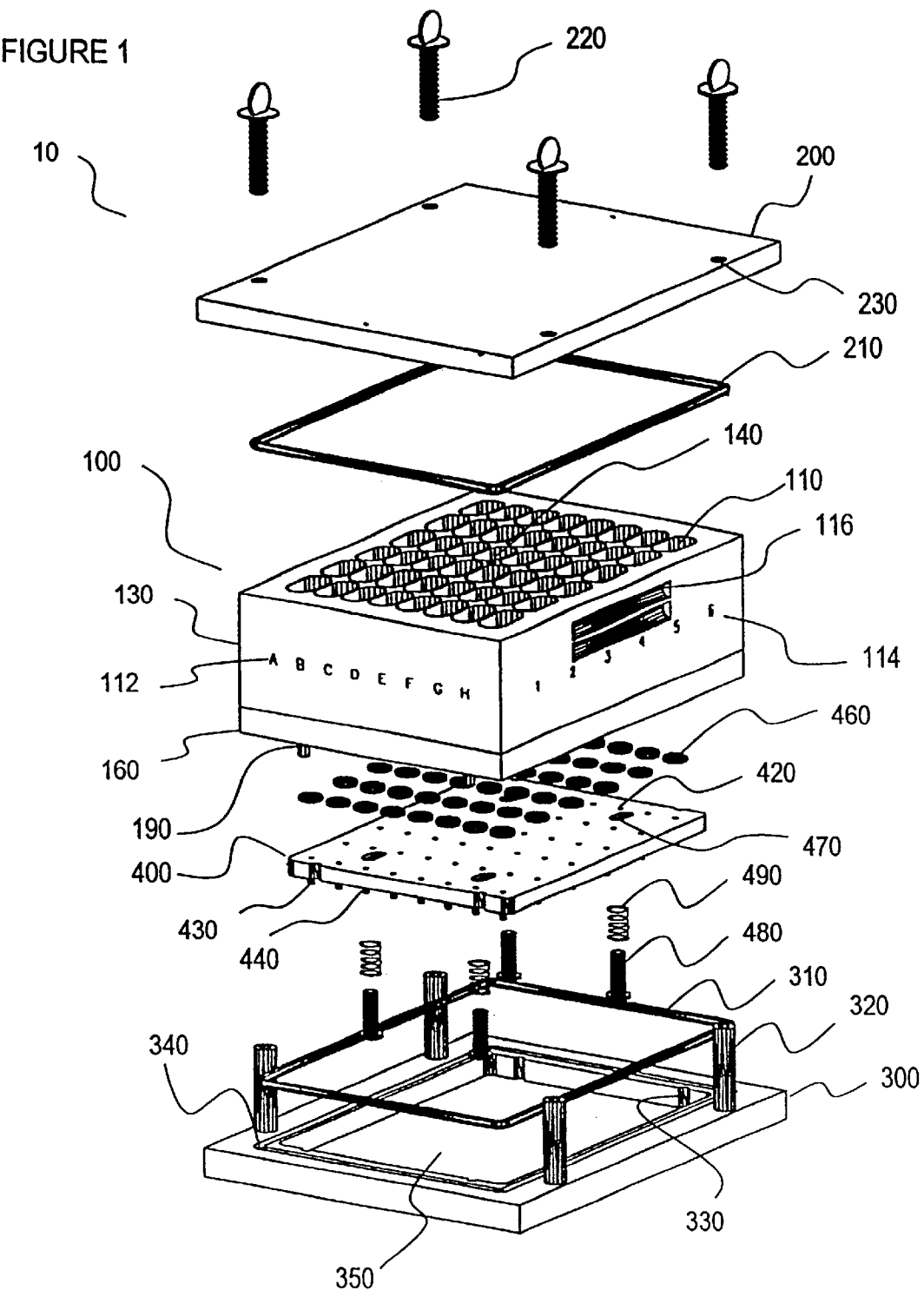
FIG. 1 is an exploded, isometric drawing of a reaction block assembly of the invention according to a preferred embodiment.

The structure and function of the preferred embodiments can best be understood by reference to the drawings. It will be noted that the same reference numerals appear in multiple figures. Where this is the case, the numerals refer to the same or corresponding structure in the figures. It should further be noted that many of the general functions and operations described below in connection with particular embodiments of the apparatus of the present invention may be realized equally well by a number of alternative mechanical designs that will suggest themselves to those of skill in the art. Such functionally equivalent alternatives, similar in concept but different in mechanical detail, are within the scope of the present invention.

FIG. 1 is an exploded isometric drawing of a 48-vessel reaction block assembly 10 with its associated reaction block cover plate 200 and baseplate 300. More particularly, in this preferred embodiment, each of the 48 vessels or chambers 110 in reaction block 100 has a nominal useable liquid volume of 3 mL. The volume generally will range from about 0.1 to about 20 mL. The reaction blocks of the present invention generally contain from about 12 to 96 or more reaction chambers. The reaction blocks are desirably sized to correspond to a standard microtiter-plate format with a footprint of 3⅜" by 5". Porous frits 500, typically plastic, may be located at the bottom of each reaction vessel and serve to retain a support resin while solvents and reagents are forced out of the chamber through a plurality of reaction vessel drain tubes 440 by application of a pressure difference across the reaction vessel. The pressure difference may result from (i) applying a positive pressure above the reaction vessel, (ii) applying a negative pressure or partial vacuum beneath or downstream of the reaction vessel (i.e., by aspiration), or (iii) by applying both a positive pressure above and a negative pressure beneath the reaction vessel.

Reaction block 100 may be machined from a single piece of stock and optionally surface-treated or coated as described further below. Preferably, the block is assembled from separate reaction block top and bottom pieces 130 and 160, respectively, to simplify the machining and/or coating operations and reduce the cost of manufacture. When the reaction block is assembled from multiple pieces, it is critical that all joints between reaction block pieces are fluid-tight. This can be accomplished by any of several means, e.g., by sealing all joints with gaskets or other sealing means by applying suitable adhesives (e.g., epoxies) at critical joints, and/or by depositing polymeric films or coatings to the surfaces to be joined—namely, the bottom surface of reaction block top piece 130, and the top surface of reaction block bottom piece 160—and then heating the coated pieces under compression to fuse the polymer coatings at the joint.

Figure 2A:
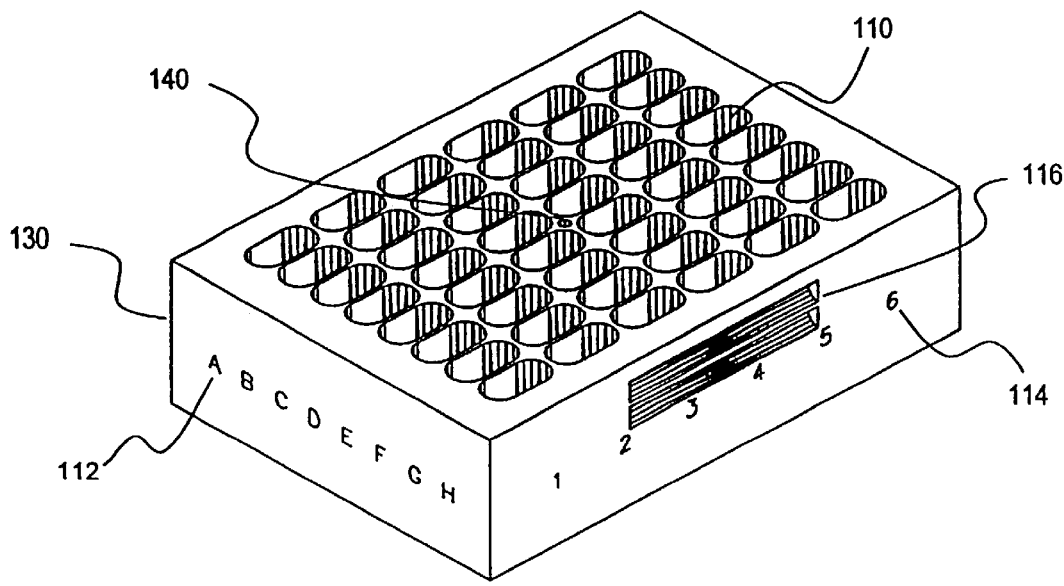
FIGS. 2A and 2B are top and bottom isometric drawings of a reaction block top piece according to a preferred embodiment.

FIG. 2A is a top-view isometric drawing of reaction block top piece 130 according to a preferred embodiment wherein the reaction block is of two-piece construction. Reaction vessels or chambers 110 extend throughout top piece 130 in this design, as does reaction block pressure-equalization/ purge hole 140 (discussed in detail below). Also shown are optional reaction vessel row identifiers 112 (typically, letters) and column identifiers 114 (typically, numbers) which may be stamped or milled into the sides of the reaction block top piece. The identifiers can be chosen to correspond to the row letters and column numbers used to identify individual wells in microtiter plates. Grips or "handles" in the form of recesses 116 can be milled into opposite sides of reaction block top piece 130 to facilitate picking up and moving the reaction block from one location to another.

Figure 2B:
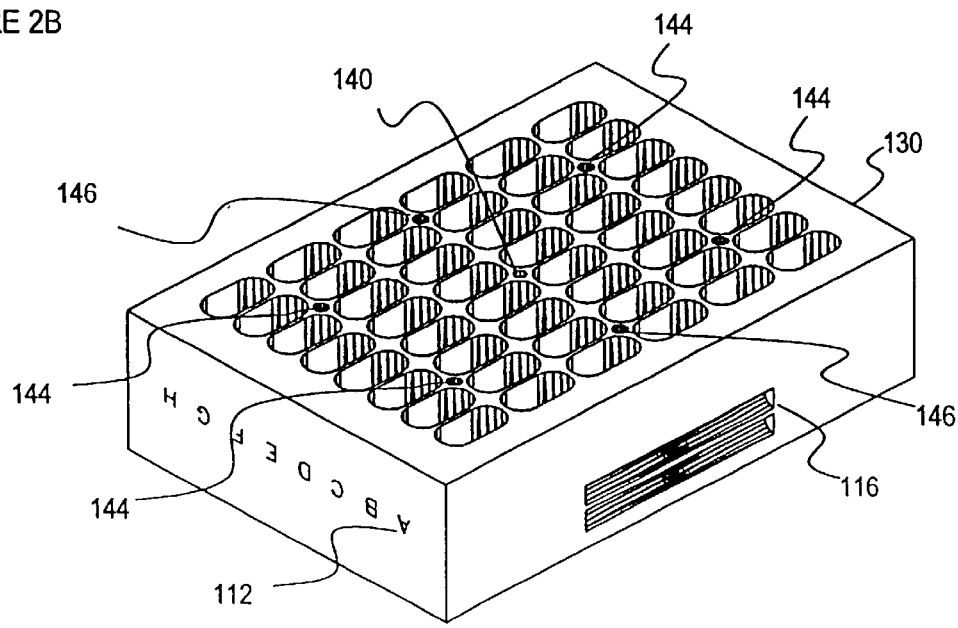

FIG. 2B provides a bottom-view isometric drawing of reaction block top piece 130 and shows several optional "blind holes" that may be drilled into the bottom surface of top piece 130. One or more reaction block fastener holes 146, which may optionally be threaded, is provided to assist in mechanically joining reaction block top piece 130 to bottom piece 160. A plurality of sliding seal plate post anchor holes 144 (optionally threaded) may serve to receive and fix one end of sliding seal plate posts 480.

Figure 3A:
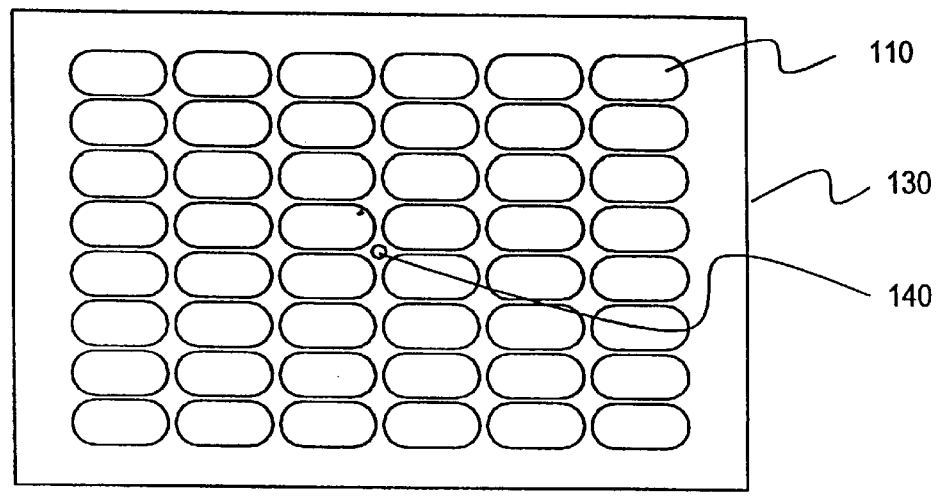
FIGS. 3A and 3B are top and bottom views of the reaction block top piece shown in FIGS. 2A and 2B.
Figure 3B:
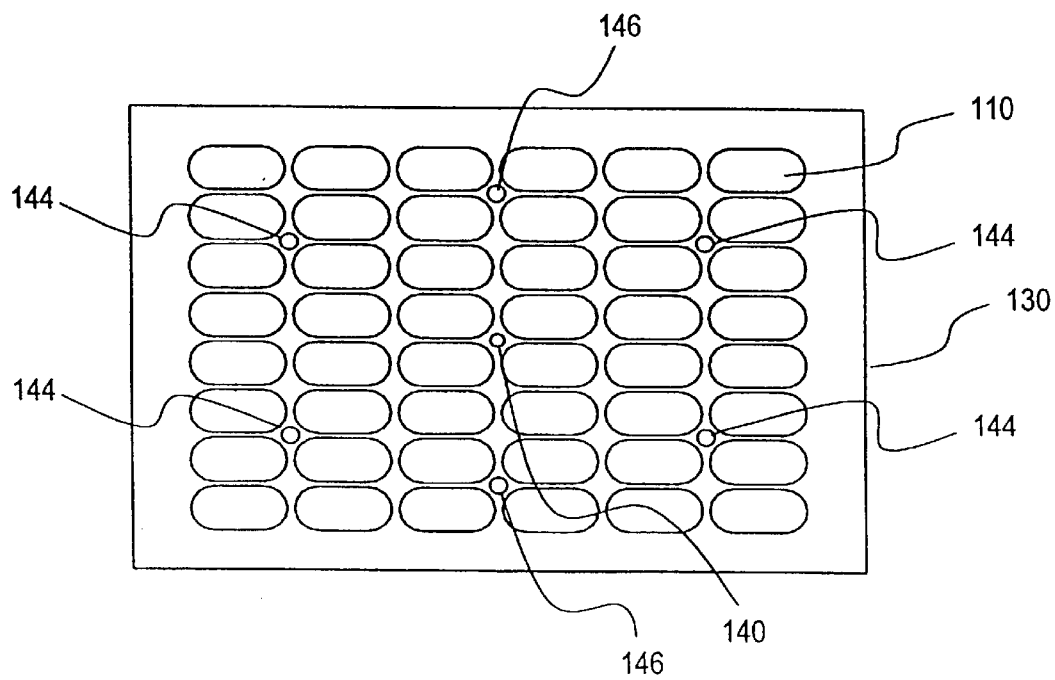

A top view of reaction block top piece 130 according to this preferred embodiment is provided in FIG. 3A, whereas FIG. 3B provides the corresponding bottom view.

Figure 4A:
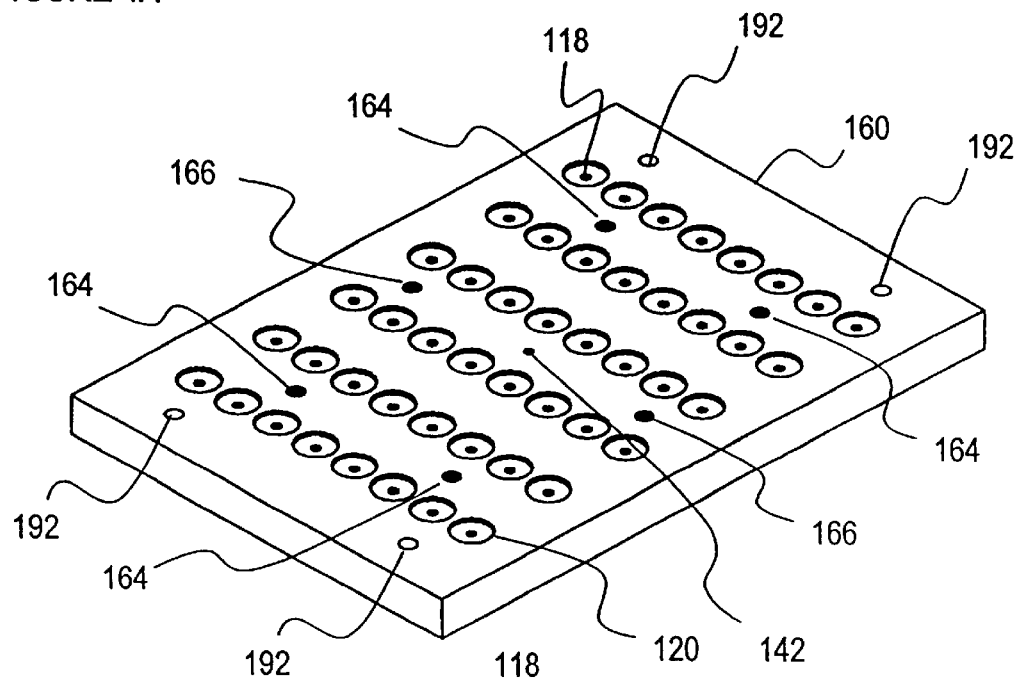
FIGS. 4A and 4B are top and bottom isometric drawings of a reaction block bottom piece according to a preferred embodiment.

Reaction block bottom piece 160 is viewed from above in FIG. 4A and from below in FIG. 4B. Reaction vessel drain holes 118 are laid out in a regular pattern (eight by six, in this case) corresponding to the layout of reaction vessels 110 in reaction block top piece 130. Surrounding each of these drain holes 118 are reaction vessel bottom recesses 120, which serve to provide space into which fluid emerging from porous frits 500 may enter and leave via the drain holes. Pressure-equalization/purge hole 142 extends through reaction block bottom piece 160 and is surrounded by concentric reaction vessel O-ring seal groove 312 where the hole emerges from the underside of piece 160 (see FIG. 3B). In a preferred embodiment, a recessed area 162 is provided on the underside of reaction block bottom piece 160 to accomodate sliding seal plate 400, among other things.

Figure 4B:
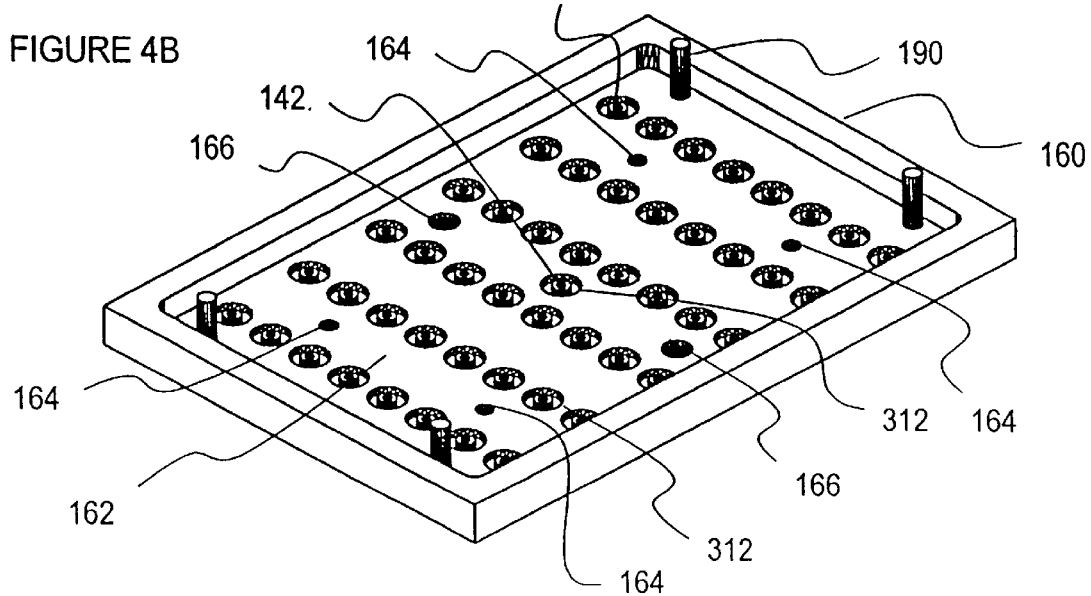
Figure 6A:
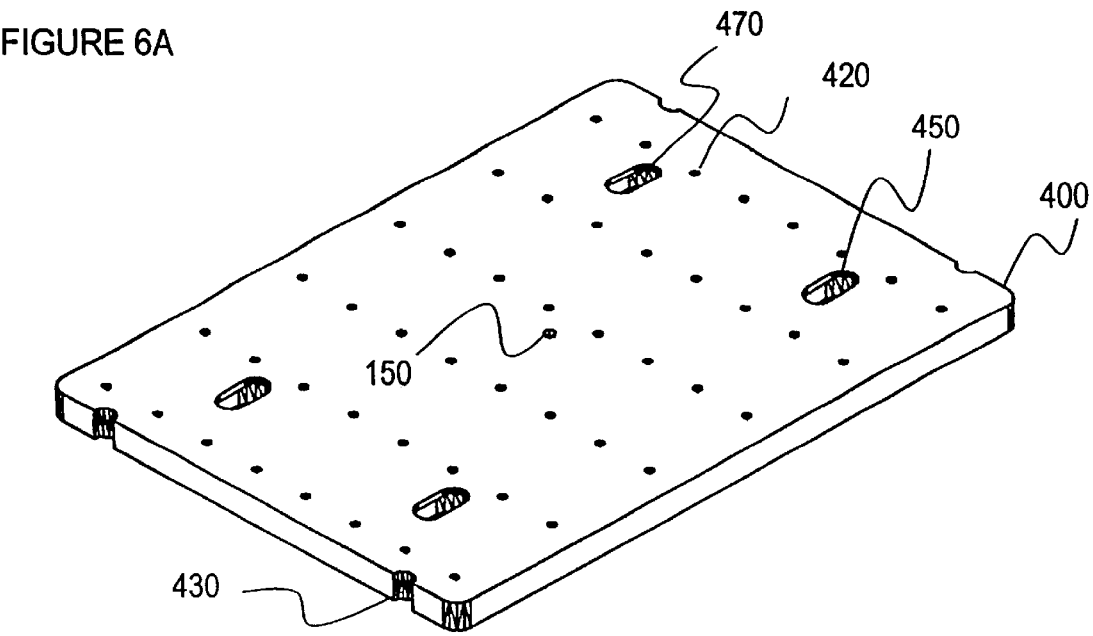
FIGS. 6A and 6B are a top and bottom isometric drawing of the sliding seal plate with fitted reaction vessel drain tubes according to a preferred embodiment.
Figure 6B:
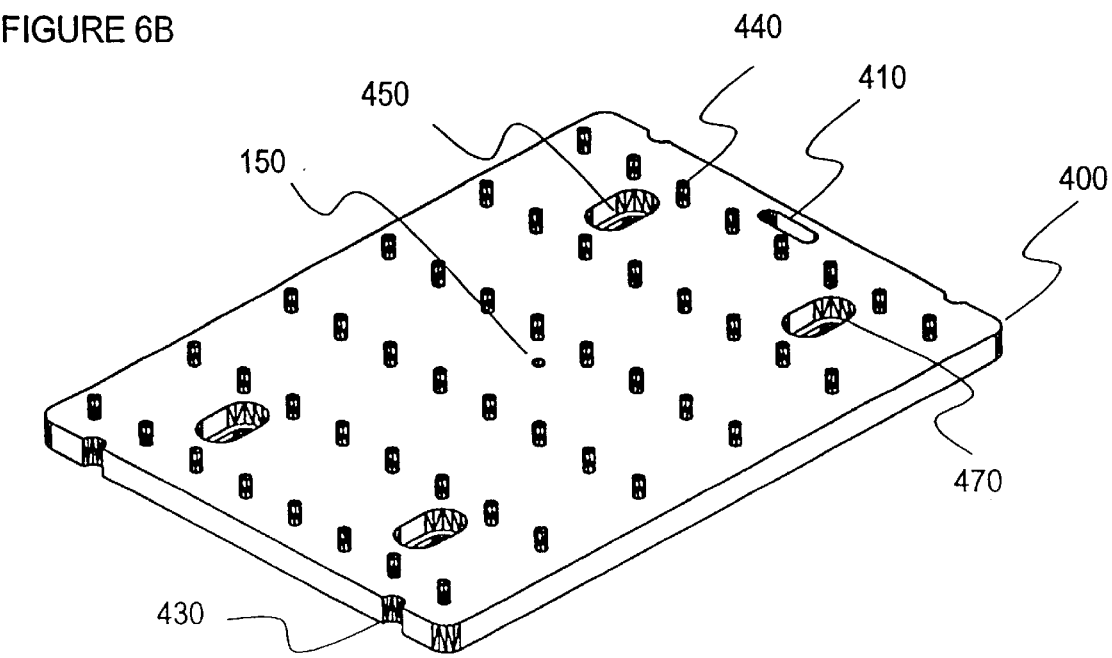
Figure 7A:
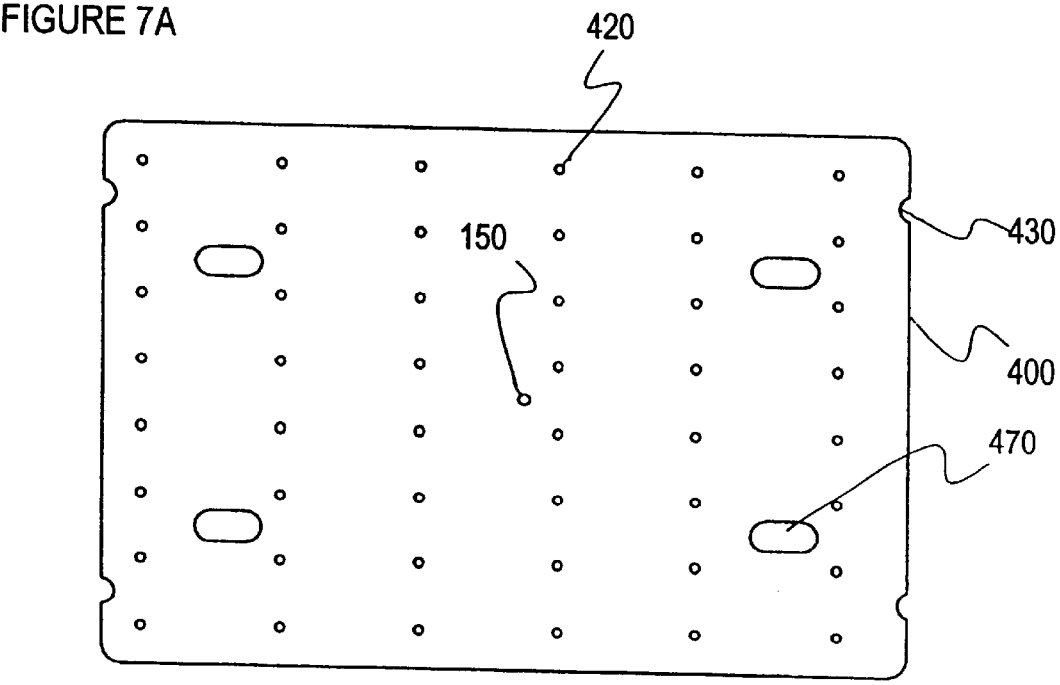
FIGS. 7A and 7B are top and bottom views of the sliding seal plate shown in FIGS. 6A and 6B.
Figure 7B:
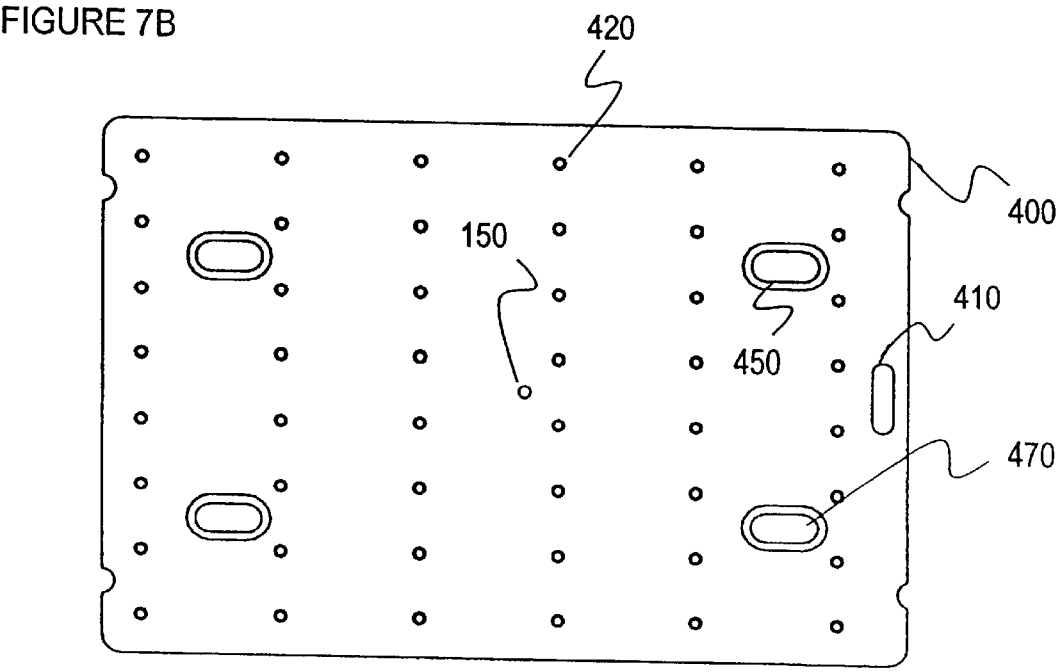

Reaction block locator pin anchor holes 192 are evident in the top surface of piece 160 (see FIG. 4A), while FIG. 4B shows locator pins 190 anchored into the holes 192. The locator pins or feet can be secured into the anchor holes by means such as threaded holes and pins, adhesives, and/or press-fitting of the pins into their corresponding holes. FIGS. 4A and 4B also show seal plate post through-holes or anchor holes 164 and reaction block fastener holes 166 extending through lower piece 160. Where fastener hole 166 emerges from the underside of lower piece 160, the hole may optionally be beveled as shown to accept the tapered head of a Phillips-type fastener.

While reaction block 100 may be constructed from a variety of materials including, but not limited to, various solvent-resistant plastics (e.g., polytetrafluoroethylene, polypropylene, and the like), preferably it is a metal (e.g., stainless steel and aluminum alloys). A preferred metal is 6061-T6 aluminum alloy which is readily machined and which exhibits a high thermal conductivity. Reaction blocks fashioned from metals will typically be machined, whereas reaction blocks fashioned from polymeric materials can be either machined or molded. Where needed, various components of the reaction block and other pieces of the reaction block assembly can be joined to one another using any suitable fastener, adhesive, braze, solder, or other joining and fabrication material and method well known in the art.

Reaction blocks fashioned from aluminum alloys are preferably post-treated after machining by anodization to apply either a conventional or "hard-coat" aluminum oxide-based surface film. Anodization can not only improve the chemical and scratch-resistance of the reaction block but also impart various colors to the block to modify its appearance. A thin coating of a solvent-resistant polymer can be applied to the external surfaces of the metal reaction blocks, including aluminum blocks whether previously anodized or not. Suitable coating techniques include powder coating, dip coating, and other methods well known in the art. One or multiple layers may be applied. Preferred polymers and copolymers are selected from the group of fluorocarbons including PTFE Teflon®, FEP Teflon®, Kel-F®, and PFA® perfluoroalkoxyethylene polymers. The coatings typically range from 2–3 to 100 microns in thickness, are chemically inert, and provide a non-reactive reaction vessel surface. They offer a layer of chemical protection to the underlying substrate against aggressive and corrosive chemicals that may be present from time to time within the reaction vessels. A particularly preferred coating material is FEP Teflon® which may be sprayed onto machined, anodized aluminum reaction block components, and then subjected to elevated temperature to form a thin, continuous film.

Reaction block top piece 130 and bottom piece 160 may be joined together by (i) coating each with FEP Teflon® polymer, (ii) pressing the pieces together with screw-type fasteners placed in reaction block top piece and bottom piece fastener holes 146 and 166, respectively, as well as with temporary fasteners in corresponding holes 144 and 164), and (iii) heating the assembly to an elevated temperature sufficient to fuse the polymeric coatings.

Referring now to FIGS. 5A, 5B, 5D, and 5E, a particularly advantageous feature of the present invention relates to the means by which the reaction vessel drainage holes 118 beneath the porous frits 500 at the base of each of the reaction vessels 110 are opened and closed to drain or retain fluids, respectively. Positive closure of the holes is achieved through a sliding seal plate 400 that is held in close proximity to and coplanar with the base of the reaction block 100 (or reaction block bottom piece 160).

As shown in more detail in FIGS. 6A, 6B, 7A, and 7B, the seal plate 400 is perforated by a plurality of through-holes 420 in the same pattern as and with the same spacing as, i.e. spatially corresponding to, the reaction vessel drain holes 118. Reaction vessel drain tubes 440 are generally short lengths of tubing pressed into or otherwise fixed within the through-holes 420 in the seal plate 400. The reaction vessel drain tubes 440 extend some distance (e.g., ¼") beyond the bottom of the seal plate and serve to direct fluids being discharged from the reaction chambers. The drain tubes 440 prevent droplets of discharged fluid from adhering to and moving along the bottom surface of the seal plate when slid.

Three or more reaction block locator pins 190 (e.g., see FIGS. 1 and 4B) typically extend from the base of the reaction block 100 (and, in a preferred embodiment, from reaction block bottom piece 160) for a distance at least slightly greater than that which the reaction vessel drain tubes 440 extend from the base. This permits these pins to serve as "feet" to support the reaction block, thereby permitting it to be placed on a surface without damaging the array of protruding drain tubes 440. The pins 190 can also serve as locator pins to ensure that the reaction block 100 is properly aligned with and thus properly mates with other reaction block accessory components such as the reaction block baseplate 300, washing plate 600 (e.g., see FIG. 11), and transfer box cover plate 820 (e.g., see FIG. 14) as described further below.

Seal plate 400 further contains a plurality (typically, four) of elongated seal plate post cut-outs 470 which may consist of elongated holes or through slots. Referring to FIG. 1, optionally adjustable seal plate posts 480 protrude through seal plate post cut-outs 470 and are optionally provided with an equal number of seal plate springs 490 which serve to push the seal plate up in the direction of reaction block 100. Each seal plate post 480 is optionally threaded to permit it to be secured into the bottom surface of reaction block 100—e.g., by passing it through or screwing it into through-hole or threaded hole 164 (e.g., see FIG. 4B) in reaction block bottom piece 160, and optionally further into threaded holes 144 (e.g., see FIG. 2B) in the bottom surface of reaction block top piece 130. Several variations on this design are obviously possible, including (a) securing the seal plate posts only in reaction block bottom piece 160, (b) passing the seal plate posts through through-holes 164 in the reaction block bottom piece 160, and then securing the post only in reaction block top piece 130, and (c) securing the seal plate posts by means of a press-fit and/or by the use of adhesives.

Preferably, the opposite (i.e., unsecured) end of each seal plate post 480 is accessible from the underside of sliding seal plate 400 and adjustable, e.g., by provision of a screw slot in the head of the post, for the purpose of adjusting the compression of spring 490. In a more preferred embodiment, seal plate post 480 is constructed of two parts—(i) a first part that is secured into the reaction block as described above and that has an axial, internally threaded hole at its opposite end, and (ii) a second, externally threaded part that may be screwed into the hole of the first part to various depths thus providing a basis for adjusting the compression of spring 490. This post-in-a-slot design limits the sliding motion of the seal plate to a single axis, (e.g., the direction parallel to the long dimension of the elongated holes or slots (i.e., cut-outs 470) which, generally speaking, will also be the direction parallel to the longer dimension of the reaction block. The limited travel of posts 480 within cut-outs 470 serves as a "stop" to limit the extent of the sliding motion of seal plate 400, typically to a travel of about ¼–½". In normal operation, the seal plate posts 480 will press up against one end or the other of the cut-outs 470 in the seal plate. Thus the sliding seal plate will be positioned at one of the two extreme limits of its motion—one limit corresponding to a "vessel-open" position to permit reaction vessels 110 to be drained (see FIGS. 5A and 5B), and the other to a "vessel-closed" position that permits the contents of the reaction vessels to be retained (see FIGS. 5D and 5E).

FIGS. 5A and 5B depict sliding seal plate 400 in its "vessel-open" position, i.e. seal plate through-holes 420 are in alignment with reaction vessel drain holes 118. In this condition, the contents of reaction vessels 110 can be drained (either to waste or to a microtiter plate) by applying a pressure difference across the reaction vessels. Fluid thus expelled from a reaction vessel 110 passes in turn through (a) optional porous frit 500, (b) reaction vessel drain hole 118 in the base of reaction block 100, and (c) the corresponding through-hole 420 in seal plate 400, finally to emerge from reaction vessel drain tube 440 protruding from the base of the sliding seal plate.

Leakage of fluid through the narrow gap between the top surface of sliding seal plate 400 and the bottom surface of reaction block 100 (and, in a preferred embodiment, the bottom surface of reaction block bottom piece 160) is prevented by an array of elastomeric reaction vessel O-ring seals 460 that bridge and seal the gap. In a preferred embodiment each of 48 O-rings 460 are located coaxially with and between (i) each of 48 reaction vessel drain holes 118 in the base of reaction block 100 and (ii) each of the 48 through-holes 420 in sliding seal plate 400. The O-rings are maintained under a modest degree of compression (e.g., about 5 to 40%) by seal plate springs 490 or by other compression means. Preferably the seal plate springs are mounted on the shaft of seal plate posts 480 and retained there, e.g., by a relatively large-diameter head of the fastener assembly that comprises the seal plate posts. The opposite end of each seal plate spring is in contact with and exerts a force against a landing or "lip" 450 (e.g., see FIGS. 5B, 5E, and 6B) which serves as a bearing surface and which is machined into seal plate 400 as a part of the seal plate post cut-out 470. Compression of seal plate springs 490 between the heads of seal plate posts 480 and seal plate post cut-out lips 450 results in seal plate 400 being forced towards the bottom surface of reaction block 100. In a preferred embodiment, reaction vessel O-ring seals 460 are located in circular reaction vessel O-ring grooves 312 (e.g., see FIG. 4B) that are milled into the base of reaction block 100. The seals remain fixed with respect to reaction block 100 even as seal plate 400 slides back and forth between its limits corresponding to "vessel-open" and "vessel-closed" positions.

Referring now to FIGS. 5D and 5E, when seal plate 400 is positioned in the "vessel-closed" or left-most limit of its sliding motion, the seal plate through-holes 420 are out of alignment with the reaction vessel drain holes 118 and no fluid communication can be established therebetween. More particularly, when seal plate 400 is in the "vessel-closed" position, the bottom surfaces of the reaction vessel O-rings 460 are in contact with solid areas of sliding seal plate 400 rather than being located coaxially with seal plate through-holes 420 as shown in FIGS. 5A and 5B, thereby effectively closing off reaction vessels 110 and preventing drainage of fluid therefrom.

The apparatus of the present invention makes it possible both to open and to close off the fluid flow path in a very positive and reliable manner to effect either drainage or retention of reaction vessel contents. The sliding seal plate of the present invention provides a sure and convenient means of closing off each and every reaction chamber with one simple mechanical action—namely, sliding of a seal plate between limits or stops.

Solvents, reagents, solutions, and/or other chemicals (e.g., catalysts and other reaction auxiliaries) may be added to the individual reaction vessels of a reaction block either manually (e.g. by pipette or other type of single- or multi-channel liquid dispenser) or with the aid of semi-automated or automated equipment (e.g., robotically). For instance, to facilitate automation of liquid dispensing, up to 8 reaction blocks can be held in place on customized racks within the workspace of a Gilson 215 Liquid Handler (Gilson, Inc., Middleton, Wis.). Generally, the reaction block will be open to the atmosphere during addition of reagents, solvents, and the like. However, highly volatile, reactive and/or noxious chemicals can be added through a perforated top cover plate and a sheet of inert septum material. Preferably, the septum material is held between two perforated top cover plates.

A particularly advantageous feature of the present invention relates to the means by which the reaction block is securely, simply, and reliably sealed off. A user may wish to isolate the contents of reaction vessels from the environment, i.e. to minimize or prevent the loss of solvent and/or reactants from reaction vessels in situations when solvents and/or reagents are volatile and/or where elevated temperatures are used. Alternatively isolation can prevent contamination when oxygen- or moisture-sensitive reagents and reactions are being conducted. Both the top and the bottom of the reaction block must be sealed off to achieve the isolation. In so doing, however, it is important to avoid establishing excessive pressure differences that might cause leaks.

In what immediately follows, we describe the situation wherein which reagents, solvents, and the like are added to individual reaction vessels prior to placing the reaction block cover plate in place. Subsequently, we describe the use of optionally perforated reaction block cover plates and septum sheets to seal a reaction block from the atmosphere.

Figure 8A:
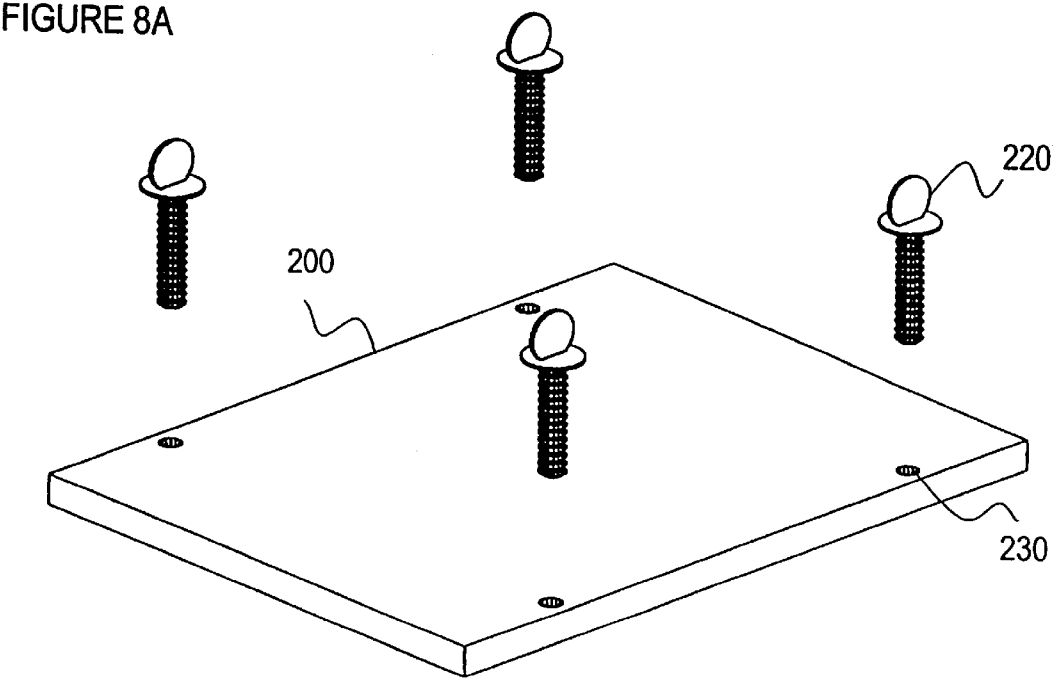
FIGS. 8A and 8B are top and bottom isometric drawings of a reaction block cover plate according to a preferred embodiment.
Figure 8B:
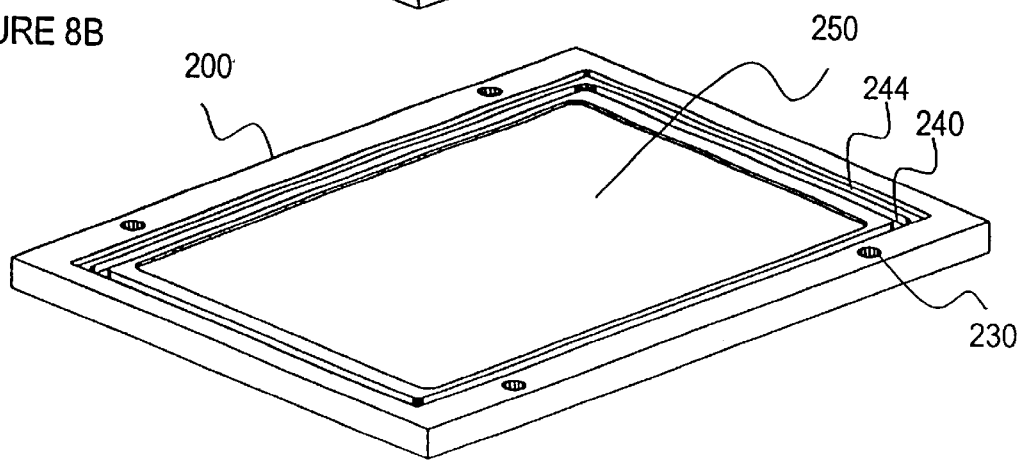

Referring to FIGS. 1, 8A, and 8B, the top seal between reaction block 100 and reaction block cover plate 200 is achieved by means of a single cover plate seal 210—typically, an O-ring or gasket—that runs completely around the perimeters of the reaction block and its cover plate. Where both mating surfaces (i.e., both the top surface of reaction block 100 and the bottom surface of top cover plate 200) are flat, a "picture-frame" gasket cut or molded from an elastomeric material suffices to seal the top cover plate. An O-ring seal 210 is employed in the preferred embodiment of FIG. 1, and thus an O-ring groove 240 is provided for this O-ring either in the top surface of reaction block 100 or, even more preferably, in the bottom surface of cover plate 200 as shown in FIG. 8B. Also shown in FIG. 8B is recess 244, which may optionally be cut into the underside of cover plate 200 in a milling operation. The top of reaction block 100 is only slightly smaller than this recessed area and thus just fits within it, the lip of the recess serving as a locating means that helps position the cover plate squarely and positively upon the reaction block. Other equivalent locating means (e.g., protrusions from the underside of the cover plate) may serve equally well in this function.

Figure 9:
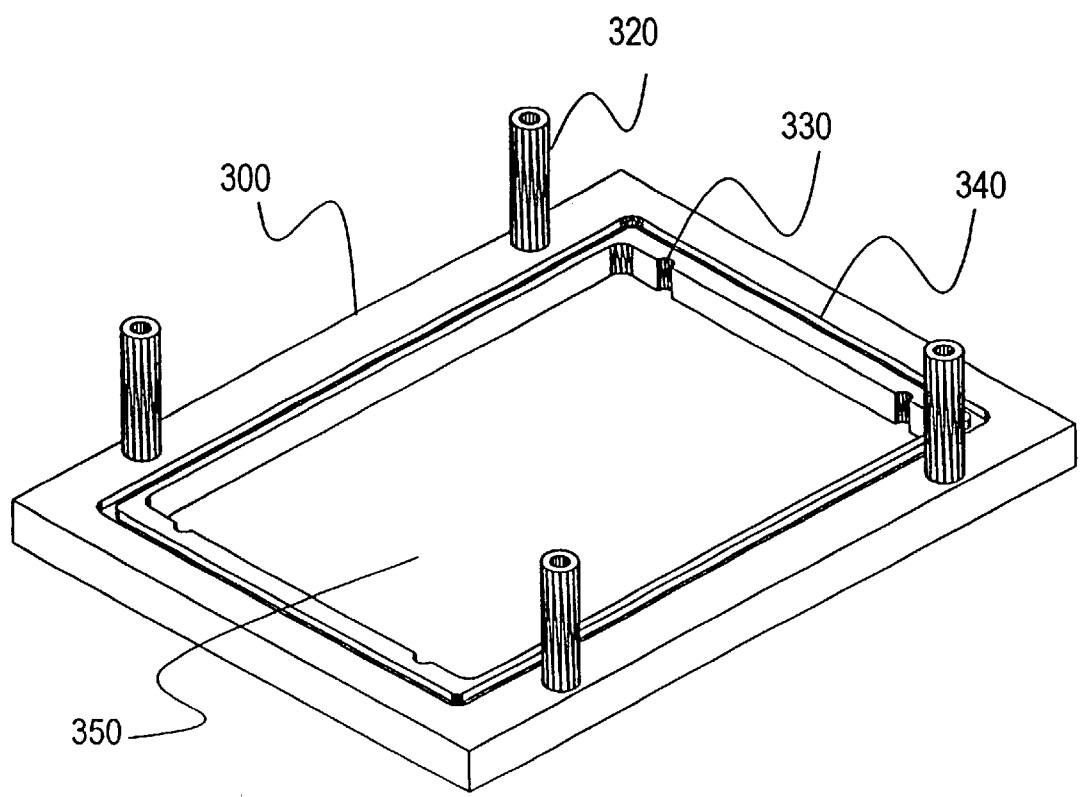
FIG. 9 is an isometric drawing (top-view) of a reaction block baseplate according to a preferred embodiment.

Reaction block assembly clamping or closure means—typically, screw or bolt-type fasteners 220, which pass through reaction block closure means through-holes 230 in cover plate 200—are used (e.g., in conjunction with reaction block assembly closure posts 320 as shown in FIG. 9) to pull the top cover plate down onto the reaction block and thereby effect a tight seal. The precise means of clamping the reaction block assembly together is not critical. What is important is that the top seal be gas- and vapor-tight at internal reaction block pressures which can be as high as several atmospheres and that the seal be reliable and convenient to establish.

Two features of the apparatus of the present invention contribute to effecting the top seal in a convenient and reliable fashion. First, the top seal in the present invention is obtained by relying upon a narrow O-ring or picture-frame gasket, either of which concentrates the compressive sealing force upon a relatively narrow region or band between the reaction block and the cover plate. Second, the reaction vessels are sealed as a group rather than individually. This contrasts to prior art reaction block designs (e.g., those offered by Advanced ChemTech, Ontogen, Robbins Scientific, and Charybdis Technologies), which employ septa or flat elastomeric sheets of material of dimensions comparable to those of the reaction block and cover plate to seal each and every reaction vessel simultaneously and independently. It can be difficult with the prior-art designs to compress the sealing material uniformly and effectively over its entire surface. This is aggravated by the fact that the total length of troublesome seal that must be established is relatively long. The length of the seal needed with the present invention corresponds merely to the perimeter of the block—and not to the product of the number of reaction vessels times their individual perimeters as in the prior-art designs.

A small space or gap is generally provided between the top surface of the reaction block 100 and the underside of cover plate 200 to permit fluid communication (i.e., at least a potential for flow) within the gas and vapor space above individual reaction chambers 110. This space or gap can be created either by intentional milling it into the cover plate or top surface of the reaction block or by the O-ring or gasket seal occupying enough space to prevent the reaction block and its cover plate from directly contacting one another. The former approach is preferred. As shown in FIG. 8B this may be accomplished by milling a recessed area 250 in the underside of reaction block cover plate 200. This construction facilitates equalization of pressures within individual reaction vessels and it facilitates equalization of pressures in the reaction block assembly above and beneath the reaction vessels. Also it permits purging of the gas and vapor space above the contents of the reaction vessels with inert gases (e.g., $N_2$, He, and Ar) where non-reactive atmospheres are required.

When highly volatile, noxious, and/or sensitive reactants or solvents are used, it will be necessary or at least desirable to dispense these reactants and/or solvents to individual reaction vessels while the vessels are closed off from the atmosphere and/or isolated from one another. Such closure and isolation can be achieved by means of an elastomeric septum (e.g., a rectangular rubber sheet) comprised of a suitably solvent-resistant material which is compressed between the top surface of the reaction block and the bottom surface of a suitably perforated cover plate. The septum sheet serves to seal the top edges of the individual reaction vessels. The holes or perforations in this cover plate are located so as to be in alignment with the openings of the individual reaction vessels, thereby permitting a reagent- or solvent-dispensing syringe needle or septum-piercing cannula to be passed first through the holes in the perforated cover plate and then through the septum material and into the space within the reaction vessels. With this two-component (i.e., plate and septum) cover plate assembly, the reaction block can be "closed" against the atmosphere while volatile, noxious, and/or sensitive reagents and solvents are dispensed into the reaction vessels. One or more syringe needles or cannula may address the reaction vessels of the reaction block simultaneously, with the identity and amounts of fluids to be delivered—and the mechanical control of the dispensing means—being optionally placed under the control of a robotic liquid handler or other type of semi-automated or automated fluid delivery equipment.

Figure 18A:
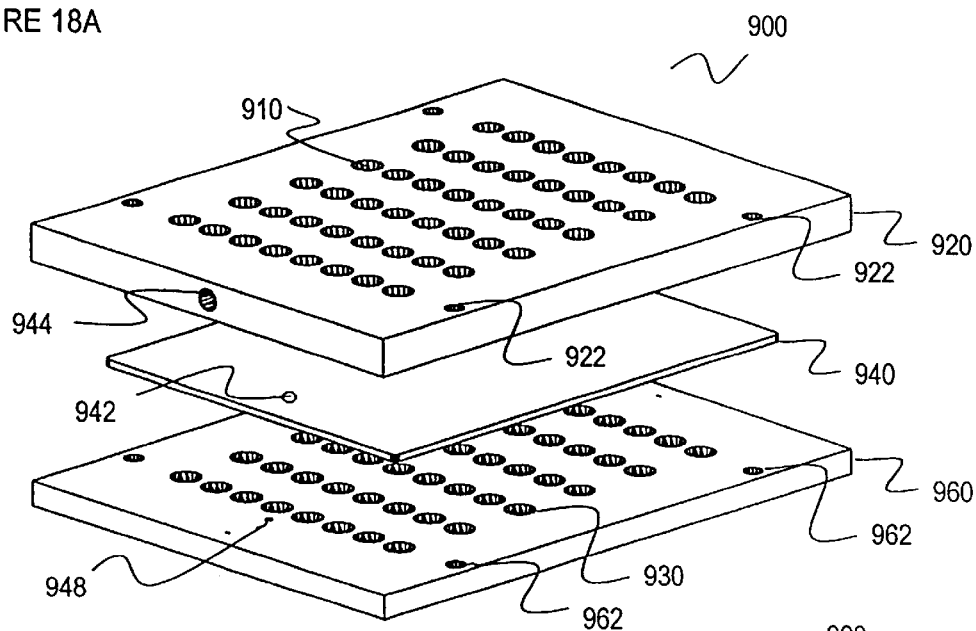
FIGS. 18A and 18B are top and bottom isometric drawings, respectively, of a perforated cover plate assembly according to a preferred embodiment.
Figure 18B:
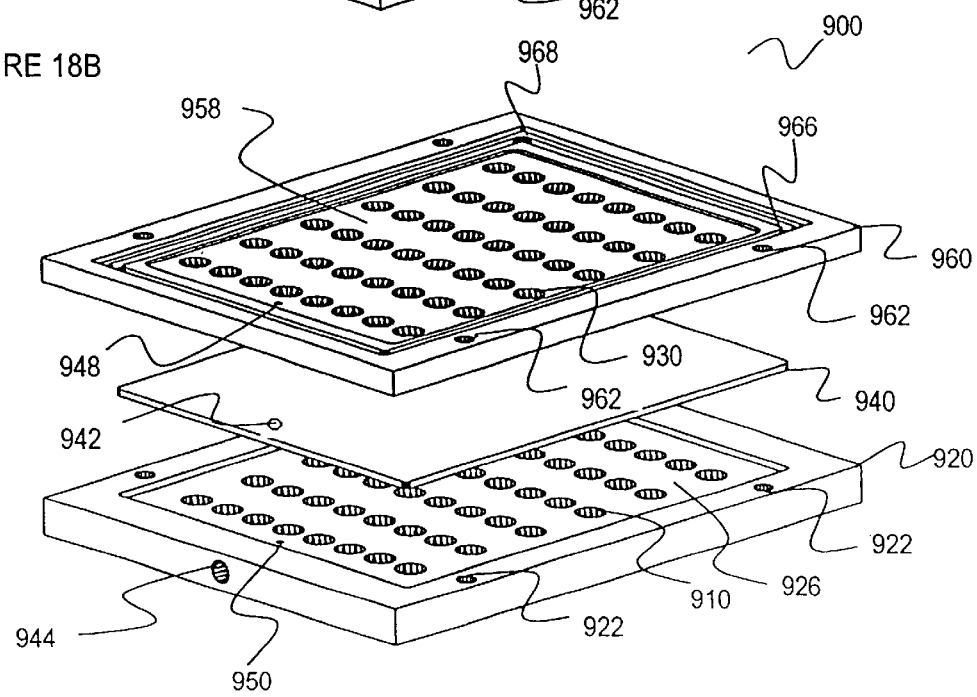

FIGS. 18A and 18B are top and bottom isometric drawings, of a particularly advantageous three-component perforated cover plate assembly 900 comprised of perforated cover plate top piece 920, septum sheet 940, and perforated cover plate bottom piece 960. Perforations 910 and 930, which extend through both perforated cover plate top piece 920 and bottom piece 960, respectively, are vertically aligned with one another—and they are further aligned with the centers of the reaction vessels 110 underlying them. This permits a syringe needle to be passed in turn through perforation 910, septum sheet 940, and perforation 930 for the purpose of delivering reagents and other solutions to the reaction vessels.

In this embodiment, the septum sheet is sandwiched or clamped between perforated cover plate top piece 920 and bottom piece 960, and the septum sheet may optionally reside within recessed area 926 milled into the bottom surface of perforated cover plate top piece 920. Top and bottom pieces 920 and 960 are, in turn, held in place atop reaction block 100 with the aid of perforated cover plate closure means (e.g., threaded fasteners similar to reaction block closure means 220 shown in FIG. 1) that extend through closure means through-holes 922 and 962 in perforated cover plate top and bottom pieces 920 and 960, respectively. Sealing is effected by means of an O-ring or other perimeter seal (e.g., a gasket) placed between perforated cover plate bottom piece 960 and the upper surface of reaction block 110. FIG. 18B shows a view of this perforated cover plate assembly 900 from below; in this view, perforated cover plate O-ring groove 966 is visible. FIG. 18B further illustrates that the underside of perforated cover plate bottom piece 960 may optionally be provided with a recess 968, a lip or ledge, or some alternative functionally equivalent "stop" means near its outside edge. In a preferred embodiment, the top of reaction block 110 fits within the recess 968, helping to locate perforated cover plate assembly 900 squarely and positively upon it.

Septum sheet 940 may optionally be provided with through-hole 942 depending on how the cover plate assembly is to be used. When the septum sheet 940 either has no through-hole 942—or where the sheet is rotated 1800 from the orientation in FIGS. 18A and 18B, the "cover-without-purge", function of this three-component perforated cover plate assembly is identical to that of the two-component (i.e., plate and septum) assembly described earlier.

When, however, it is desired to access the reaction vessels via syringe and simultaneously purge the reaction block, e.g., with an inert gas, a perforated septum sheet 940 with through-hole 942 is preferably employed. The desirability of purging and the means by which it is achieved in the present invention are discussed in considerably more detail below. (See, for example, the parts of this specification describing the design and use of pressure-equalization/purge holes 140, 142, and 150 as shown, for example, in FIGS. 5A, 5C, 5D, and 5F). Proper placement of septum sheet 940 with through-hole 942 within perforated cover plate assembly 900 makes it possible to either supply or remove purge gas from the top compartment of the reaction block via cover plate top piece purge gas access hole 944.

This particular "cover-and-purge" embodiment of the invention relies on through-hole 942 being positioned in vertical alignment with both cover plate top piece purge gas collection/distribution hole 950 and with bottom piece purge gas through-hole 948. Purge gas collection/distribution hole 950 and cover plate top piece purge gas access hole 944 are in fluid communication with one another, so that gas that flows in hole 944 flows out hole 950 and vice versa. Recessed area 958 is provided on the underside of perforated cover plate bottom piece 960 as shown in FIG. 18B to permit purge gas as well as other gases and vapors to flow through the space above the reaction vessels (hereinafter referred to as the "top compartment") within the reaction block assembly and to permit "pressure equalization" to occur.

It will also be desirable if not necessary to seal the bottom of the reaction block from the atmosphere during reactions conducted with volatile chemicals and/or at elevated temperatures. Referring now to FIGS. 1 and 9, in a preferred embodiment the perimeter seal between the bottom surface of reaction block 100 and the top surface of reaction block base plate 300 is made with an O-ring or picture-frame gasket seal 310 (e.g., see FIG. 1) that concentrates the compressive sealing force upon a relatively narrow region of these surfaces. O-ring seal 310 is shown residing in baseplate O-ring groove 340 in FIG. 9. Other features of reaction block baseplate 300 include reaction block locator pin recesses or cut-outs 330 to accomodate the locator pins 190 protruding from the bottom of the reaction block—as well as provision for recessed area 350, which can optionally be milled into the top side of reaction block baseplate 300. This recessed area 350 affords sufficient space to accomodate the sliding seal plate 400, seal plate posts 480, reaction block locator pins 190, and reaction vessel drain tubes 440.

The top and bottom seals—in combination with upper and lower chamber pressurization equalization means—dramatically reduce the burden placed on individual reaction vessel O-ring seals 460, thereby improving their reliability.

At times in a multistep synthesis (e.g., when washing a resin or cleaving compounds from a support), it will be necessary that the space above the reaction vessels (i.e., the "top compartment") and the space below the reaction vessels (hereinafter referred to as the "bottom compartment") be isolated from one another. For instance, to expel the contents of the reaction vessels by applying a pressure difference across the chambers, it is necessary that the top and bottom compartments be separated such that the only possible fluid flow path between compartments is through the individual reaction vessels, through reaction vessel drain holes 118, and ultimately out reaction vessel drain tubes 440. At other times (e.g., when heating the reaction block), it is desirable that the pressures in the compartments above and below the reaction vessels be equal to eliminate any pressure difference that might cause leakage of fluids from the reaction vessels.

This can be illustrated with reference to prior-art reaction block designs. For instance, in the reaction blocks exemplified by the Advanced ChemTech Model 396 synthesizer and Ontogen's U.S. Pat. No. 5,609,826, a plurality of S-shaped trap tubes serves, in effect, as a bank of siphon-type valves that attempts to control drainage of solvents and reactants from individual reaction vessels. If, however, a pressure difference is established between the top and bottom compartments of these prior-art reaction blocks which is of a magnitude sufficient to push liquid out of a reaction vessel and into the top of the trap tube, then the siphoning action of the trap tube will be initiated and substantially all of the liquid in the reaction vessel will ultimately be drained from the reaction vessel. This siphon action is desirable, of course, during resin washing; however, the uncontrolled emptying of reaction vessels by inadvertent priming of their respective siphons is highly undesirable when it takes place unexpectedly during reaction steps. In effect, the siphon-type trap tubes of these prior-art reaction block designs have a limited capability to remain appropriately "closed" in the face of pressure differences that may be established between the top and bottom compartments, e.g., by uneven heating of the reaction block or by partial vaporization of reaction vessel contents. Inadvertent drainage of reaction vessel contents, especially during reactions, has constituted a heretofore unsolved and important problem in reaction block design.

In contrast, a particularly advantageous feature of the sliding seal plate design of the present invention is its provision of a much more robust and reliable means of closing (and, when desired, opening) the reaction vessel drains. The reliability of the reaction vessel closing means of the present invention is enhanced by minimizing the pressure difference established between top and bottom compartments and, hence, across individual reaction vessel O-ring seals 460, as taught further below.

In a preferred embodiment, equalization of top- and bottom-compartment pressures is accomplished by pressure-equalization means comprised, for example, of a fluid channel or communication path that is provided between these respective compartments. This fluid communication channel is conveniently opened, thereby equalizing pressures and all but eliminating any pressure difference when desired. The channel is just as conveniently closed during incubation or reaction steps. In a particularly preferred embodiment, the fluid communication channel responsible for pressure equalization comprises appropriately sized holes drilled vertically through the sliding seal plate and the reaction block, respectively. FIGS. 2A, 2B, 3A, and 3B show reaction block top piece pressure-equalization/purge hole 140, while FIGS. 4A and 4B show bottom piece pressure-equalization/purge hole 142. It should be noted that pressure-equalization/purge holes 140 and 142 are one and the same where reaction block 100 is of single-piece as opposed to two-piece construction. FIGS. 6A, 6B, 7A, and 7B illustrate corresponding pressure-equalization/purge hole 150 drilled through sliding seal plate 400. Reaction vessel O-ring seal 460 located in reaction vessel O-ring seal groove 312 in the underside of reaction block bottom piece 160 (e.g., see FIG. 4B) seals the gap between the bottom surface of bottom piece 160 and the top surface of seal plate 400.

FIGS. 5C and 5F illustrate the spatial relationship between the pressure-equalization/purge holes 140 and 142 in reaction block 100 and pressure-equalization/purge hole 150 in sliding seal plate 400 when the seal plate is in "vessels-open" and "vessels-closed" positions, respectively. In particular, when it is desired to equalize top and bottom component pressures (as it is, for instance, during reaction steps), sliding seal plate 400 is positioned at its left-most, "vessels-closed" position as shown in FIGS. 5D, 5E, and 5F. In this position reaction vessel drain holes 118 are closed off by the seal plate as discussed above. However, in this position pressure-equalization/purge hole 142 in reaction block bottom piece 160—and, for that matter, pressure-equalization/purge hole 140 in top piece 130—are brought into vertical alignment with pressure-equalization/purge hole 150 in sliding seal plate 400 (see FIG. 5F).

Once a reaction step has been completed, the reaction vessel drains are opened to remove unconverted reactants and waste products and, in subsequent steps, wash solvent. The top and bottom compartments must be isolated at this point so that a pressure difference can be established across the reaction vessels. This is accomplished by sliding seal plate 400 to its right-most, "vessels-open" position as shown in FIGS. 5A, 5B, and 5C wherein reaction vessel drain holes 118 are in vertical alignment with the corresponding seal plate through-holes 420 and reaction vessel drain tubes 440. At the same time, however, pressure-equalization/purge hole 142 in reaction block bottom piece 160 is brought out of alignment with pressure-equalization/purge hole 150 in sliding seal plate 400 (see FIG. 5C) so that the top and bottom compartments are isolated and a pressure difference can be established across the reaction vessels to promote drainage of liquid contents.

The pressure-equalization means is particularly critical when the reaction block assembly is heated to incubate otherwise slow chemical reactions and/or when volatile reactants, reagents, or solvents are employed. When the reaction block assembly is sealed to retain volatile contents, the internal pressures in the top and bottom compartments can increase significantly with the heating. Although the pressures increase, they generally do not do so at equal rates. Rather, a pressure imbalance would occur, resulting in inadvertent and premature drainage of reaction vessel contents. This undesirable outcome is prevented by the pressure-equalization means of the present invention which assures that pressures in the top and bottom reaction block compartments increase (and, upon cooling, decrease) at precisely the same rate. By equalizing the pressures in the top and bottom reaction block compartments, the pressure difference that the reaction vessel O-rings must withstand is significantly reduced, thus improving system reliability.

Thus, in a preferred embodiment of the invention, the pressure-equalization means represented by the reaction block pressure equalization/purge holes 140 and 142 and by the seal plate pressure-equalization/purge hole 150, the reaction block cover plate O-ring seal 210, the baseplate O-ring seal 310, and the individual reaction vessel O-ring seals 460 all work in concert as an integrated system. Their effect is to contain solvents and reactants within the reaction vessels, to contain gases and vapors within the top and bottom compartments of the reactor block assembly, and to exclude atmospheric constituents (e.g., $O_2$ and $H_2O$ vapor) from the interior of the reaction block assembly—all in a highly reliable and convenient manner.

Yet another desirable feature of the present reaction block assembly enabled by the channel comprised of pressure-equalization/purge holes 140, 142, and 150—and the system used to bring these holes into and out of alignment, as appropriate—is the ability to purge the top and bottom compartments of the reaction block assembly with an appropriate gas or gas mixture. This feature is useful where one wishes (i) to exclude and/or flush atmospheric contaminants (e.g., $O_2$ and $H_2O$ vapor) from the reaction block assembly and provide an inert gas atmosphere, (ii) to flush volatile reaction byproducts from the assembly, and/or (iii) to supply reactive gases to the reaction (e.g., oxygen or air for oxidation reactions, or hydrogen for catalytic hydrogenations). This purge function is enabled by the same system of pressure-equalization/purge holes discussed above and by provision of appropriately located purge gas inlet and exit ports, e.g., on reaction block solid and perforated cover plates 200 and 900, on wash plate 600, and/or on baseplate 300.

For instance, in one method for purging the reaction block, the reaction vessel drains are closed and pressure-equalization/purge holes 140, 142, and 150 are opened prior to and/or during reaction steps. Thus, when it is desired to purge during a reaction, this permits a flow of purge gas to be established through the reaction block assembly. More particularly, purge gas flows (i) into a gas inlet port located on baseplate 300 or washplate 600, (ii) through the bottom compartment (e.g., via baseplate recess 350 or washplate recess 660), (iii) up through the purge channel comprised of pressure-equalization/purge holes 140, 142, and 150, (iv) through the top compartment and past reaction vessels 110 (e.g., via cover plate recess 250 or 958), and finally (v) out a gas outlet port located on cover plate 200 or 900.

Other equally suitable gas flow arrangements and gas port configurations will be evident to those of ordinary skill in the art. For instance, the purge gas inlet can be located on cover plate 200 and the outlet on baseplate 300 (with the direction of purge gas flow reversed), or cross-flow of purge gas may be made to occur into and out of the top and/or bottom compartments of the reaction block assembly.

In a preferred embodiment of the invention, purge gases may be passed directly through the contents of all of the reaction vessels simultaneously, efficiently stripping undesired dissolved gases from the liquids contained therein and saturating the liquids with inert purge gases and/or gaseous reactants. In this instance, the sliding seal plate is moved to its "vessel-open" position once purge gas pressure and flow are established, which action also closes off the alternative gas flow path represented by through-holes 140, 142, and 150. As shown in FIGS. 5A and 5C, this action forces purge gas supplied to the bottom compartment of the reaction block assembly to pass upwards through the reaction vessel drainage path comprised of reaction vessel drain tube 440, seal plate through-hole 420, reaction vessel drain hole 118, and porous frit 500—the purge gas emerging from the frit as bubbles that promote efficient gas/liquid mass transfer (i.e., either stripping of undesired gases and/or saturation with desired ones) within reaction vessels 110. Purge gas then passes through the top compartment of the reaction block assembly via reaction block solid cover plate recess 250 or perforated cover plate recess 958 and ultimately emerges through a purge gas outlet port on the cover plate (e.g., purge gas access hole 944.

Purging may be effected before and/or during a chemical reaction step. For instance, it will frequently be desirable to purge the reaction block assembly and/or reaction vessels for a short period before initiating the chemical reaction to flush contaminants from the system. After contaminants are expelled, air- or moisture-sensitive reactants can then safely be added to the reaction vessels, e.g., with the aid of a septum-piercing syringe and perforated cover plate assembly 900. Moreover, purging will often be continued throughout the reaction step to keep the system contaminant-free and/or to maintain a supply of reactant gas. The continual purging can be effected either through the reaction vessels themselves with the sliding seal plate remaining in its "vessel-open" position or through the pressure-equalization/purge channel comprised of holes 140, 142, and 150, with the sliding seal plate moved to its "vessel-closed" position.

In yet another method of operation, a positive pressure of purge gas may be trapped within the reaction block assembly by closing off the purge gas exit and inlet ports, thus permitting the system to be tightly sealed during a subsequent reaction step. The latter two modes of operation minimize evaporation of solvent from the reaction vessels.

Prior-art reaction block designs—including those of Advanced ChemTech, Ontogen, Robbins Scientific, and Charybdis Technologies—do not permit purging of gases from one reaction block compartment to another in the manner of the present invention. The prior-art designs either make no satisfactory provision for the supply of gases to and from reaction vessels or permit only dead-ended gas flow for the purpose of pressurization and reaction vessel drainage, as opposed to reaction block purging.

Finally, it will be apparent that the reaction block assembly of the present invention can also be vented (as opposed to purged) through the above-mentioned fluid communication system. This can be useful, for example, where it is desired to limit the internal pressure established within the reaction block assembly during reaction steps. By venting the reaction block assembly through a pressure-relief valve, excessive internal pressures that might otherwise build up and create a safety hazard during reactions can be avoided. Additionally, by providing pressure-control means (e.g., a mechanical back-pressure regulator or liquid bubbler) in the purge gas exit line, one may readily control the pressure within the reaction block.

An additional safety feature of the reaction block apparatus of the present invention is the ability of the spring-loaded seal plate to release excess reaction vessel pressures. For instance, in alternative embodiments of the invention, the pressure-equalization/purge means may not be employed and/or the openings of the individual reaction vessels may be independently sealed, e.g., with a septum sheet. Under these circumstances, if for some reason one were to attempt to inject a volume of liquid into one of the sealed reaction vessels that exceeds the empty space available therein to accomodate it, then the pressure in the reaction vessel would tend to increase—occasionally with dangerous consequences—were it not for the pressure-relieving ability of the spring-loaded seal plate. With the seal plate 400 pressed against reaction vessel O-ring seals 460 by seal plate springs 490, excessive reaction vessel pressures will cause downward motion of seal plate 400, accompanied by further compression of springs 490. This downward motion will continue until the gap between the bottom surface of reaction block 100 and the top surface of seal plate 400 becomes too great for the reaction vessel O-ring seals 460 to close. At this point leakage of fluid from the reaction vessels will occur through the gap and excess pressure will be relieved.

Figure 10A:
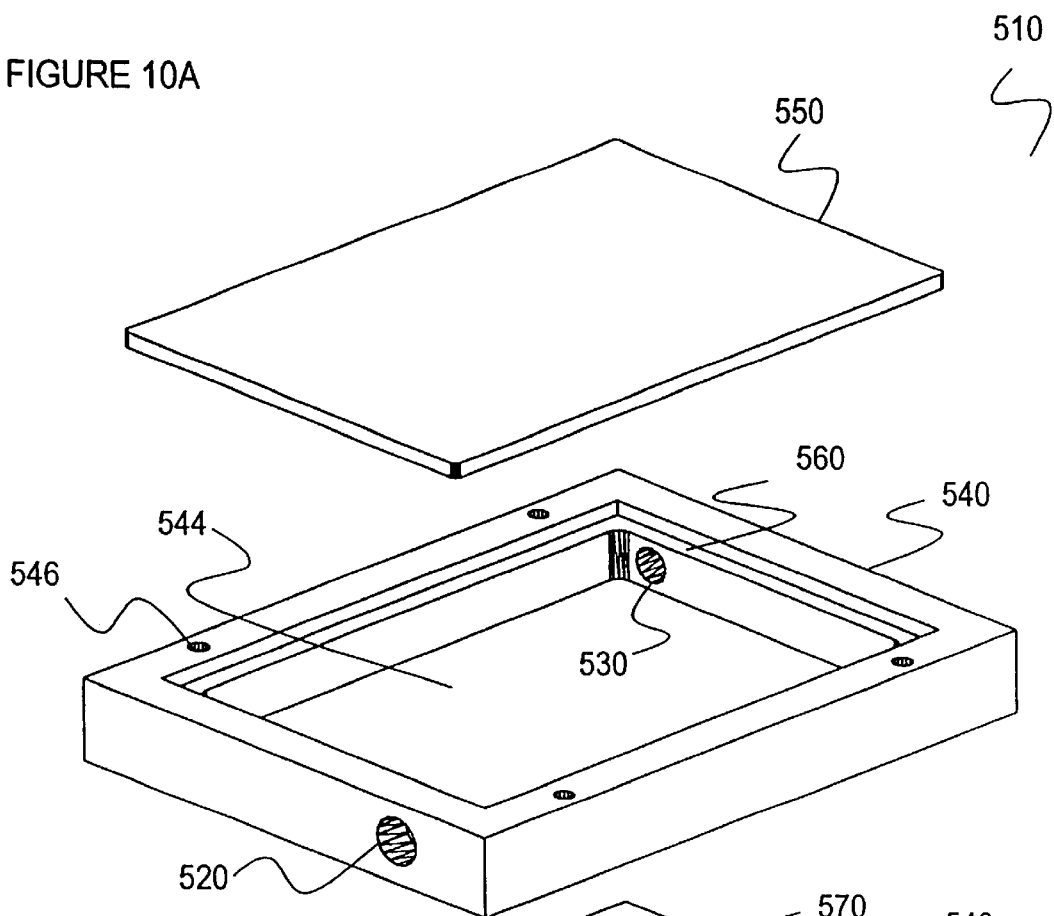
FIGS. 10A and 10B are top and bottom isometric drawings of a reaction block heat/cool cover plate according to a preferred embodiment.
Figure 10B:
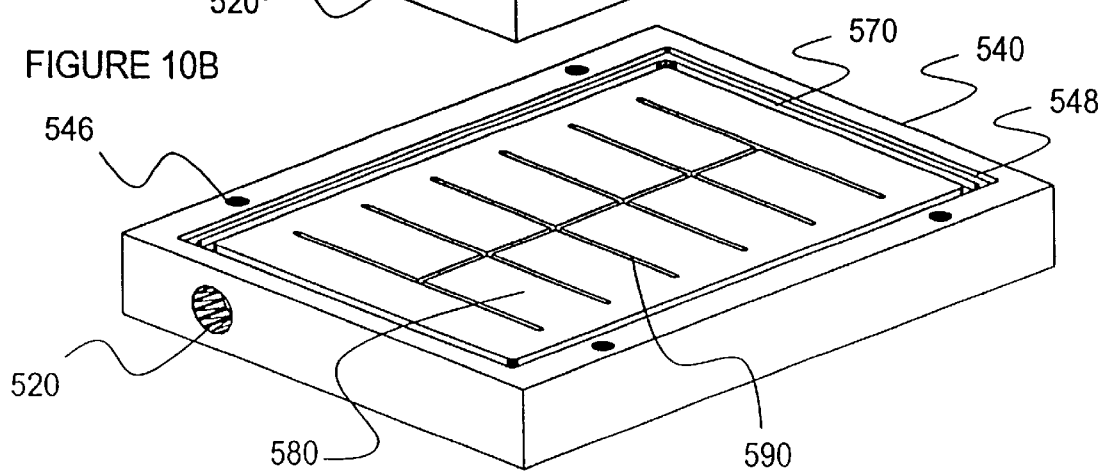

Many syntheses require that reaction temperatures be controlled either above or below ambient temperature. FIGS. 10A and 10B are top and bottom isometric drawings, respectively, of a preferred reaction block heat/cool plate assembly 510 useful for this purpose. It consists of a heat/cool cover plate box 540 containing interior passage or cavity 544 through which either hot or cold heat-transfer fluid may be passed. In one embodiment, the fluid enters heat-exchange fluid inlet port 520 and exits via heat-exchange fluid exit port 530, circulating between an external temperature-controlled circulating bath and heat/cool plate assembly 510. Feedback control of reaction block temperature may be incorporated. Heat/cool cover plate box cavity 544 may be formed by milling out a solid piece of metal stock, in which case heat/cool plate closure 550 forms the missing wall of the box; closure 550 may consist simply of a flat piece of metal that is put in place upon heat/cool cover plate closure lip 560 and affixed there by means of adhesives (e.g., epoxy), fasteners, or the like.

Heat/cool plate assembly 510 can be held firmly in place atop reaction block 100 by various means including fasteners that extend through heat/cool cover plate closure means through-holes 546 and engage, for example, reaction block assembly closure posts 320 affixed into reaction block baseplate 300. Also shown in FIG. 10B is recess 548, which may optionally be cut into the underside of heat/cool cover plate box 540 in a milling operation. The top of reaction block 100 is only slightly smaller than this recessed area and thus just fits within it, the lip of the recess thus serving as a locating means that helps to position heat/cool cover plate assembly 510 squarely and positively upon the reaction block. Other locating means (e.g., protrusions from the underside of the heat/cool cover plate box) may be used.

Ideally, heat-exchange surface 580 (i.e., the bottom surface of heat/cool plate assembly 510) will be in intimate physical and thermal contact with the top surface of reaction block 100 to promote rapid and uniform heat transfer. The objective of sealing the reaction block against the heat/cool plate while providing intimate thermal contact between these components can be achieved by using a perimeter seal which leaves no gap or empty space between the heat/cool plate and the top surface of the reaction block. In a preferred embodiment, this seal is effected by means of an O-ring that resides in heat/cool cover plate O-ring groove 570. Finally, continuous recessed areas or grooves 590 are provided in heat-exchange surface 580 on the underside of heat/cool cover plate assembly 510 to permit fluid communication between each and every reaction vessel 110.

Figure 11:
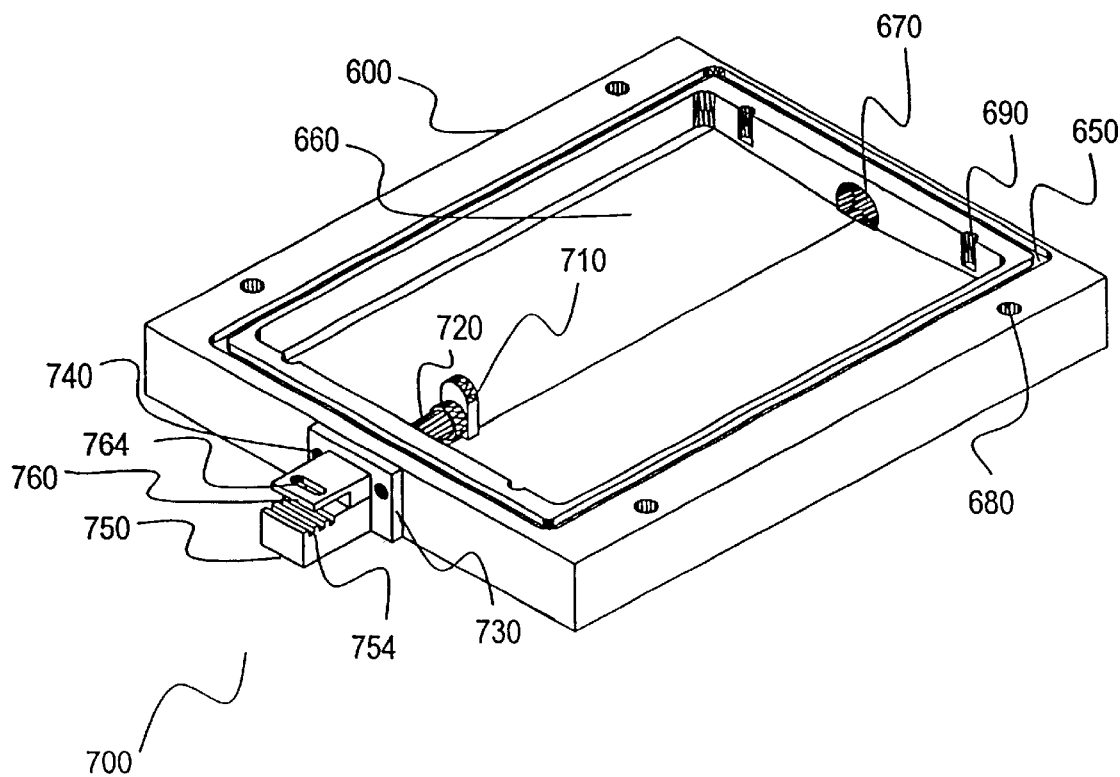
FIG. 11 is a top isometric drawing of a wash plate according to a preferred embodiment.

Washing of resin between reaction steps is facilitated in the method and apparatus of the present invention through the use of wash plate 600 as illustrated in FIG. 11. The wash plate is designed to mate with the lower surface of the assembly comprising the reaction block 100 and seal plate 400 as shown further in FIG. 12. Wash plate clamping means 610 is secured atop reaction block 100 by means of wash plate clamp fasteners 620, which extend through wash plate clamping means through-holes 630 and are secured into wash plate assembly clamping posts 640. Clamping means 610 may be, for example, an appropriately shaped metal extrusion that holds the reaction block firmly in place during the sequential resin washing operations of (a) wash solvent dispensing, (b) agitation/incubation, and (iii) removal of wash solvent (by pressurization or aspiration) from the reaction vessels. A tight seal between reaction block 100 and wash plate 600 is effected by means of a perimeter O-ring or gasket seal, preferably an O-ring seal which is seated in wash plate O-ring groove 650 as illustrated in FIG. 11.

FIG. 11 shows additional details of wash plate 600, upon which reaction block 100 and seal plate 400 rest during resin washing operations. Its central region consists largely of a recessed area or wash plate cavity 660 that is sized to accomodate the reaction block, seal plate, and their associated components and hardware; cavity 660 is in fluid communication with fluid exit port 670 which provides a route by which wash solvent may drain from the wash plate. The bottom surface or "floor" of cavity 660 may optionally be sloped inwards and/or towards one end of wash plate 600 to facilitate drainage of liquids from the interior. Fluid exit port 670 may be located either on the floor of cavity 660 (e.g., at its center or towards one end) or at one end of the wash plate as illustrated in FIG. 11. In a preferred embodiment, sliding seal plate actuator means 700 (described in more detail below) is located at an end of wash plate 600. Other features of wash plate 600 illustrated in FIG. 11 include wash plate assembly clamping post anchor holes 680 and wash plate block locator pin recesses or cut-outs 690.

Figure 13A:
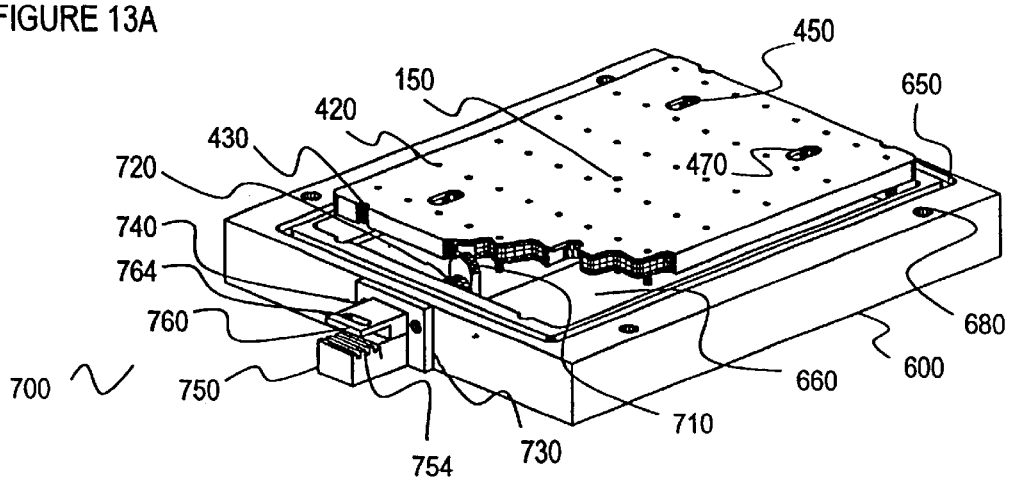
FIGS. 13A, 13B, and 13C are isometric drawings illustrating sliding seal plate actuator means 700 moving sliding seal plate 400 between its "vessel-open" (FIG. 13A) and "vessel-closed" (FIG. 13B) positions.
Figure 13B:
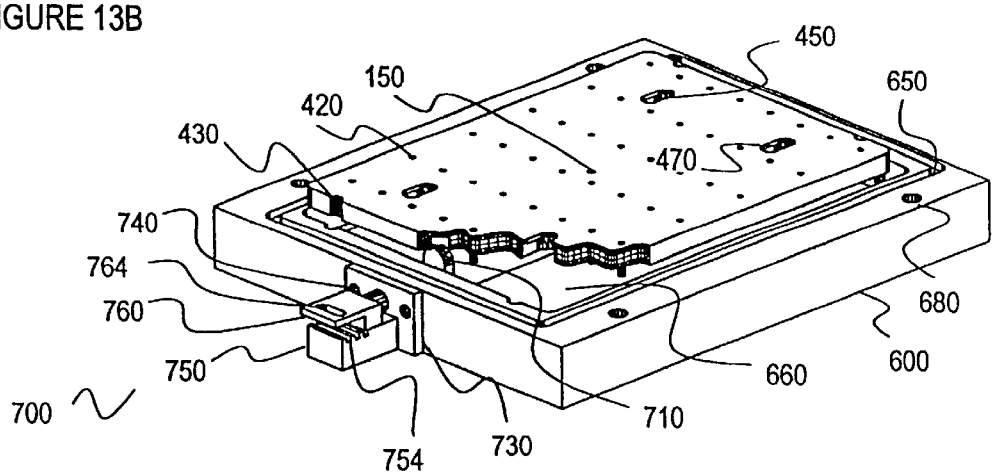

Thus far, little has been about ways in which sliding seal plate 400 may be moved between its "vessel-open" and "vessel-closed" positions. A preferred means of positioning the sliding seal plate involves the movement of seal plate actuator means 700. A preferred design of actuator means 700 is depicted in some detail in FIGS. 11, 13A, 13B, and 13C. Here, the actuator means consists of an actuator rod 720 fitted with a seal plate engaging pin 710 on one end and an actuator slide 760 on the opposite end. Engaging pin 710 fits into sliding seal plate actuator engaging pin cut-out 410 on the seal plate, the cut-out 410 being shown, e.g., in FIGS. 5C, 5F, 6B, and 7B. The positions of actuator means 700—and hence of engaging pin 710 and seal plate 400—are determined by mechanically moving slide 760 in and out of an actuator rod through-hole that passes from the exterior to the interior of wash plate 600 as shown in FIG. 13A. When slide 760 is pulled "out" (i.e., away from wash plate 600 as depicted in FIG. 13B), then sliding seal plate 400 is pulled into its "vessel-open" position as depicted in FIGS. 5A, 5B, and 5C. In contrast, when slide 760 is pushed "in" (i.e., towards wash plate 600 as depicted in FIG. 13A), then sliding seal plate 400 is pushed into its "vessel-closed" position as depicted in FIGS. 5D, 5E, and 5F.

Figure 13C:
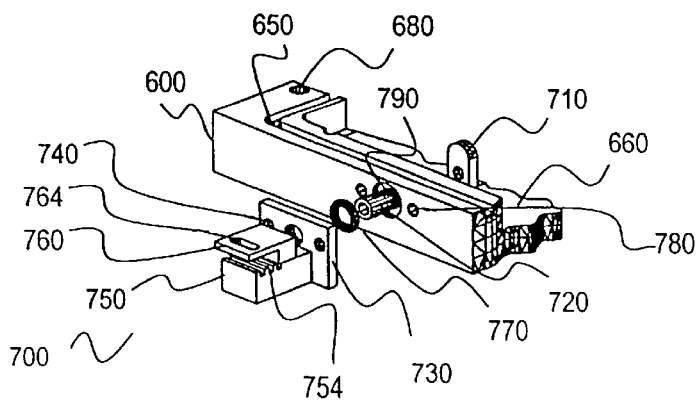

The construction of preferred actuator means 700 may be further understood with reference to the exploded view of this assembly shown in FIG. 13C. In one embodiment, actuator rod 720 is provided either with threaded holes on both of its ends or with external threads, either of which permit attachment of sliding seal plate actuator engaging pin 710 and seal plate actuator slide 760 to its opposite ends, perhaps with the aid of appropriate fasteners. Actuator rod 720 may optionally be machined so as to have two diameter—with the larger diameter end being placed inside wash plate 600 to serve, in effect, as a "stop" to limit the extent to which rod 720 may be pulled out of the wash plate. O-ring seal 770 (or other suitable seal, e.g., a rubber washer or equivalent gasket) slides onto actuator rod 720 and ensures a gas-tight seal where rod 720 passes through the wall of wash plate 600 via the through-hole provided for it; as shown in FIG. 13C, this actuator rod through-hole may optionally be provided with an O-ring groove or recess 790 that accomodates actuator rod O-ring seal 770. Seal plate actuator base 750 is mounted onto seal plate actuator attachment plate 730, and attachment plate 730 is, in turn, affixed to wash plate 600 with the aid of appropriate fasteners that extend into seal plate actuator attachment mounting plate holes 740 and actuator-assembly-to-wash-plate mounting holes 780. In a preferred embodiment, a screwdriver or other tool may be passed through slot 764 in seal plate actuator slide 760 and thence to one of several grooves 754 in seal plate actuator base 750. By prying the screwdriver or other tool in one direction or another, sliding seal plate actuator means 700 may be caused to move in and out between the limits of its motion.

For instance, the sliding motion of seal plate 400 relative to reaction block 100 (and hence opening and closing of reaction vessels 110) can be effected by any of various means. For example, in one such alternative embodiment a simple actuator mechanism uses a pair of arms or cams positioned at the lower end of each of two rotating vertical shafts (one at either end of the reaction block) which contact the sides of the sliding seal plate. Rotation of these shafts, optionally slotted to fit a screwdriver, causes the arms or cams to push against the sides of the sliding seal plate and thus effect its translation. That is, rotation of one of the actuator shafts presses the surface of its arm or cam against one end of the seal plate to cause the latter to slide in one direction and motion in the opposite direction is caused by turning a similar actuator shaft located at the opposite end of the reaction block.

In another embodiment, the sliding motion of seal plate 400 relative to reaction block 100 (and hence opening and closing of reaction vessels 110) is effected by fixing the sliding seal plate in space and then moving the reaction block in the horizontal plane. The net result is equivalent—namely, translation of the sliding seal plate relative to the reaction block.

Figure 12:
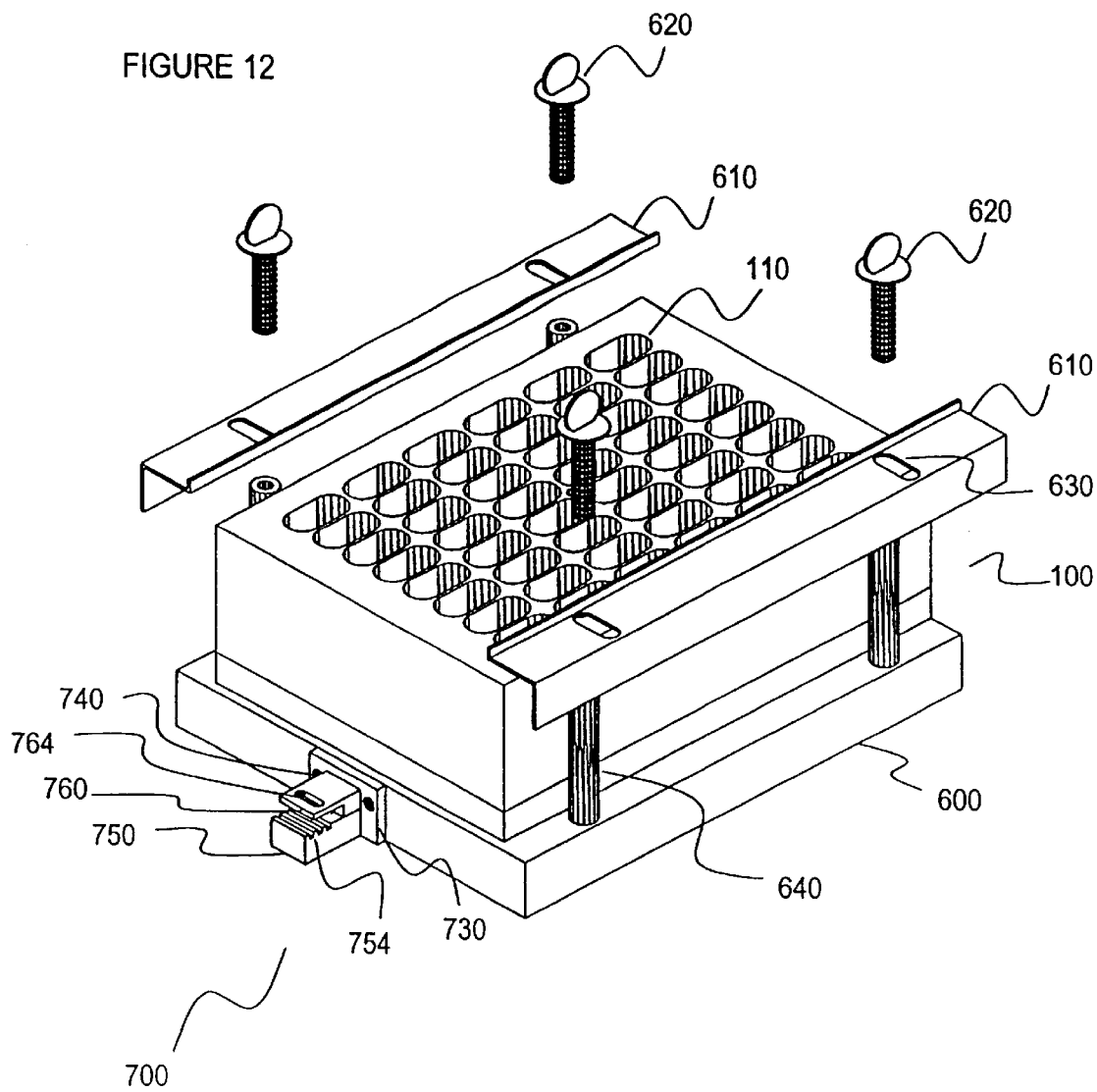
FIG. 12 is a top isometric drawing of a reaction block residing atop a wash plate as shown in FIG. 11.

During chemical reactions, sliding seal plate 400 will be located in its "vessel-closed" position. To prepare reaction block 100 for resin washing operations, cover plate 200 and baseplate 300 (if in place) are first removed, and the reaction block is placed atop wash plate 600; FIG. 12 illustrates a preferred embodiment. The perimeter of the bottom surface of reaction block 100 is then sealed against wash plate 600, e.g., by means of an O-ring or picture-frame gasket; wash plate clamping means 610 and associated fasteners (e.g., fasteners 620 and clamping posts 640) may be used to hold the reaction block tightly against the wash plate. Alternatively, spring-loaded or other clamps may be employed. When the reaction block is secure, sliding seal plate actuator means 700 is pulled away from the wash plate (e.g., by pulling on slide 760)—or alternative means of moving seal plate 400 are employed—to cause the seal plate to move from its "vessel-closed" to "vessel-open" position.

To effect drainage of liquid from the reaction vessels, a pressure difference is imposed across the reaction vessels. Pressurization requires that a cover plate (not shown in FIG. 12) be at least temporarily installed over the reaction vessels, and that certain straightforward modifications to the wash plate clamping means be made. In most cases it will be preferable to empty the reaction vessel contents by aspiration. While the pressure difference to empty the reaction vessels can be applied before or after the seal plate is slid to its "vessel-open" position, it is generally preferable to apply the pressure difference first.

In a preferred embodiment, fluid valving means will be located in the waste solvent flow path downstream from wash plate fluid exit port 670 and in close proximity to wash plate 600. This waste fluid valve will preferably take the form of a manually operated valve. When this waste fluid valve is opened, the contents of reaction vessels 110 (e.g., wash solvents) will be drained from the vessels since the sliding seal plate will be in its "vessel-open" position at this point. However, when the waste fluid valve is closed, there will be little or no liquid drainage from the reaction vessels (despite the fact that the sliding seal plate is in its "vessel-open" position) because the space downstream of the reaction vessels constitutes a closed system with very limited capacity to accept additional fluid. As soon as a small amount of liquid drains from the reaction vessels in to this closed finite volume space, there will be a tendency for the pressure in that space to increase, thus preventing further drainage of the reaction vessels.

It should be noted that although it obviously remains possible to close the reaction vessels during wash solvent addition by sliding the seal plate to its "vessel-closed" position, this action will generally be unnecessary with the preferred apparatus of the present invention. The present invention simplifies resin washing operations and their automation considerably, since it does away with the need for sliding the seal plate twice during each wash cycle. Thus needless wear and tear on the reaction vessel O-ring seals can be avoided.

When a pressure difference is established a cross the reaction block (whether by pressurization or aspiration), reactant solutions and wash solvents present in the reaction vessels are made to flow (i) through the porous frits at the base of the reaction vessels and out of the reaction block, (ii) through the open passages in the sliding seal plate, (iii) into the recessed area or cavity in the wash plate, and (iv) out the wash plate fluid exit port via waste fluid valving means and appropriate tubing that ultimately leads into a waste chemicals collection vessel or trap. When the contents of individual reaction vessels are drained by aspiration, the required partial vacuum may be supplied by a vacuum pump or aspirator located downstream of the waste chemicals collection vessel or solvent trap.

To ensure thorough resin washing, such operations will typically be conducted repeatedly. For instance, a resin wash cycle might be comprised of the sequential steps of (i) reaction vessel drainage by aspiration, (ii) wash solvent dispensing, (iii) agitation and resin incubation (to provide time for excess reactants, products, and other solution-phase reaction auxiliaries to diffuse out of the resin interior and into the wash solvent), and—once again—(iv) aspiration, thus completing a wash cycle.

In alternative embodiments, the manually operated waste fluid valve may be replaced by other pressure-actuated fluid valving means. For instance, a normally-closed, spring-loaded valve may be employed which opens only when a certain threshhold or "cracking" pressure is applied across the valve in the forward (i.e., upstream-to-downstream) direction. Or a waste fluid valve that takes the form of a siphon or S-shaped trap tube may be located downstream of wash plate fluid exit port 670. For instance, the siphon or trap tube can be mounted on a vertical extension of one end of the wash plate, or even milled into the interior of the extension as an integral component of the wash plate assembly. The alternative types of waste fluid valves will be closed when no significant pressure difference is applied across them (e.g., during wash solvent dispensing and resin agitation) but will be "open" when the liquid contents of the reaction vessels are being drained.

By employing pressure-actuated waste fluid valves of the types exemplified above (e.g., normally-closed, spring-loaded valves, siphon or S-shaped trap tubes, and their equivalents), one avoids opening and closing a manual valve to control reaction vessel drainage. Since the application of pressure or vacuum is involved in expelling the contents of the reaction vessels, it is particularly convenient to use this same pressure or vacuum source to control the state (i.e., "open" or "closed") of the waste fluid valve.

A related and novel feature of the use of a common waste fluid valve (whether manual or pressure-activated) has to do with the fact that drainage of reaction vessels is controlled via a single valving means as opposed to being controlled by a plurality of drain valves associated with each and every reaction vessel. This feature simplifies design of the apparatus and improves the reliability of fluid management during resin washing operations.

Moreover, it is significant that the common waste fluid valve of a preferred embodiment of the present invention is located separately and apart from the reaction block itself. This provides a number of degrees of design freedom that are unavailable with other prior-art designs where the means for controlling reaction vessel drainage during washing operations is an integral part of the reaction block. For instance, the use in the present invention of separate and common waste fluid valving means enables the use of valve types that could not be incorporated within the reaction block itself for various reasons (e.g., size).

The several operations involved in the resin washing cycle (namely, solvent dispensing, agitation/incubation, and vessel drainage) are tedious—and because the resin typically undergoes several cycles of washing (sometimes with different solvents) between separate steps in a chemical synthesis, it is often desirable to automate resin washing. The equipment that achieves this is referred to herein as an "automated wash station." Semi-automated or automated operation of resin washing can be accomplished by mounting a plurality of wash plates (e.g., four) with associated tubing and valves atop a mini-orbital shaker (e.g., Model 7744, BellCo Glass, Inc., Vineland, N.J.) and then placing the reaction blocks of the present invention atop the wash plates.

In a typical wash cycle, wash solvent is dispensed either with a multichannel pipettor or robotic dispenser to each of the reaction vessels; the reaction blocks and their contents are agitated for an appropriate length of time; and then wash solvent is aspirated from the reaction vessels—all of these operations optionally being placed under computer control. Semi-automated and automated wash stations of the present invention may be operated in stand-alone fashion on the combinatorial chemist's bench-top or within a fume hood. Alternatively, the wash stations can be located within the working area of an appropriately modified robotic liquid handling systems, such as the Gilson 215 Liquid Handler. Such robotic systems are capable of dispensing individual reactants to selected reaction vessels prior to synthesis as well as dispensing wash solvents during resin rinsing operations. Thus, integration of the reaction block assemblies, wash plates, and wash stations of the present invention with such robotic liquid handling systems can lead to significant productivity enhancements during all phases of combinatorial library synthesis.

In a preferred embodiment the reaction block dimensions and the layout of the individual reaction vessels within it are such as to permit the synthesized compounds (or compound mixtures) to be cleaved from the support resin and transferred directly into the corresponding wells of deepwell microtiter plates. This is very straightforward when the number of reaction vessels and their layout in the reaction block corresponds precisely to the number and layout of the wells in the microtiter plate that is to accept them. For instance, with the 48-vessel reaction block shown in FIG. 1, it is relatively straightforward to transfer compounds or compound mixtures synthesized therein to microtiter plates containing 48 wells in the standard eight-by-six configuration. Compound cleavage and transfer are facilitated through the use of a transfer box assembly that is designed to mate with the reaction blocks and to house a microtiter plate located so as to receive the compounds being transferred from the reaction vessels.

Figure 14:
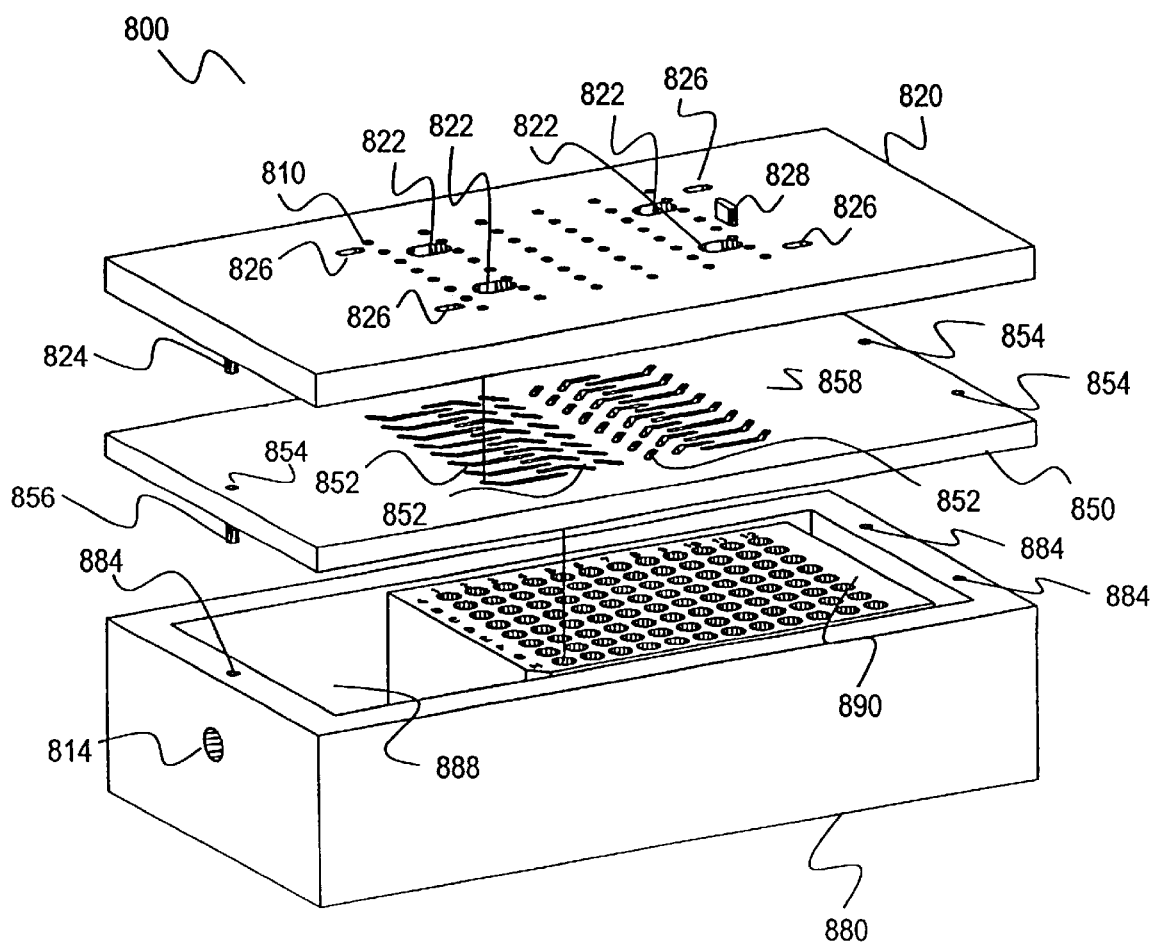
FIG. 14 is an isometric drawing of a transfer box assembly according to a preferred embodiment of the present invention.

FIG. 14 is an isometric drawing of a transfer box assembly 800 according to a preferred embodiment of the present invention. The assembly consists of a transfer box base 880, a transfer box cover plate 820, and, optionally, a transfer box reformatting plate 850. Transfer box base 880 has an internal cavity 888 sized so as to permit the placement of a deepwell or other type of receiving element, e.g., microtiter plate 890, within its interior. Alternatively, the internal cavity could hold an array of glass vials or of sorbent media, e.g. vials, columns, disks or the like. It could even hold a second reaction block assembly, esp. when the apparatus is used for solution phase chemistry as discussed below. Cover plate 820 is fitted with a plurality of transfer box cover plate locator pins 824 that fit into corresponding transfer box base locator pin holes 884 or transfer box reformatting plate locator pin holes 854, depending on the desired configuration of the transfer box assembly.

To prepare transfer box assembly 800 for cleavage and transfer of compounds from a 48-vessel reaction block to a 48-well microtiter plate—one with individual wells sufficiently large to accomodate the fluid volumes contained in the individual reaction vessels—is first placed in position within interior cavity 888 of transfer box base 880. Transfer box cover plate 820 is next set in place atop base 880, with an optional gas-tight seal between the cover plate and transfer box being established if desired (e.g., with the aid of an O-ring or other perimeter sealing means or gasket). Cover plate 820 has a plurality of holes 810 through it in a pattern that precisely matches the pattern of reaction vessel drain tubes 440 extending from the bottom of seal plate 400. Transfer box cover plate through-holes 810 may optionally be fitted with an equal number of cover plate director tubes (not visible in FIG. 14) that extend from the underside of cover plate 820.

To initiate cleavage of synthesized compounds from the solid-phase support resin, a solution of a reagent such as trifluoroacetic acid (TFA) that will break the chemical linkage between the support (or linker arm, if used) and the compounds is added to each of the reaction vessels. Of course, sliding seal plate 400 will be slid to its "vessel-closed" position prior to this operation. Next, an incubation period will optionally be provided to permit the cleavage reaction to proceed substantially to completion, thus liberating discrete library compounds (or mixtures thereof) into the solution contained within the reaction vessels.

After this incubation period, reaction block 100 is then placed atop the transfer box assembly 800. More particularly, reaction block locator pins 190 are positioned so as to enter transfer box locator pin slots 826; reaction vessel drain tubes 440 are positioned so as to enter transfer box cover plate through-holes 810, and sliding seal plate actuator engaging pin cut-out 410 is made to engage transfer box actuator pin 828. Transfer box seal plate post clearance holes 822 are located so as to accept seal plate posts 480. It should be noted that holes 822 and slots 826 are preferably "blind" holes and slots that do not extend completely through transfer box cover plate 820.

In a preferred embodiment, transfer of cleaved compounds is initiated by moving seal plate 400 to its "vessel-open" position after a suitable pressure difference is applied across the reaction block—either by pressurization (i.e., by applying a positive pressure above the reaction vessels) or, preferably, by aspiration (i.e., by applying a vacuum to the transfer box assembly, e.g., by connecting a vacuum pump to transfer box base vacuum port 814). Alternatively, the pressure difference (e.g., vacuum) can be applied after moving the seal plate to its "vessel-open" position. As discussed above in conjunction with alternative methods of moving seal plate 400 relative to reaction block 100, this relative motion is preferably effected in this instance by moving the reaction block while keeping seal plate 400 fixed in space. In particular, transfer box actuator pin 828 can be used to hold seal plate 400 in a fixed position atop cover plate 820 while reaction block 100 is manually slid across the top surface of the cover plate. This has the effect of changing the spatial relationship between the reaction block and the seal plate from the "vessel-closed" to the "vessel-open" position. (This aspect of the present invention is described further below in the discussion of FIGS. 16A and 16B.) At this point, the pressure difference across the reaction block causes the liquid contents of the reaction vessels to be expelled from the reaction block and collected in the wells of microtiter plate 890 held within transfer block base 880.

In instances where the number of reaction vessels in a reaction block does not match the number of wells in a multi-well microtiter plate, the process of compound cleavage and transfer is somewhat more complicated but can still be performed efficiently with the apparatus of the present invention. For instance, compounds (or compound mixtures) produced in and cleaved from the first of a pair of 48-vessel reaction blocks can be made to occupy half of the wells of a 96-well plate—with the remaining 48 wells later being filled with the contents of the reaction vessels in the second of this pair of 48-vessel reaction blocks.

Several variations on the transfer box apparatus design and operation are possible and within the scope of the present invention. Perhaps the simplest of these embodiments has cleaved compounds from a multi-vessel reaction block being drained into the microtiter plate wells that lie directly beneath and in vertical alignment with the director tubes that emerge from the underside of transfer box cover plate 820. For instance, where the reaction vessels of a 48-vessel reaction block are laid out in an 8-by-6 array (i.e., with the eight rows typically being designated as A through H, and the six columns being designated as 1 through 6), the spatial relationship between reaction vessels and wells in a 96-well microtiter plate will be such that cleaved compounds will be transferred into alternate columns—e.g., into either even-numbered or odd-numbered columns, depending on the position of microtiter plate 890 within cavity 888 of transfer box base 880. More particularly, compounds will be cleaved and transferred into either the odd-numbered wells (i.e., A1, A3, . . . , A11; B1, B3, . . . , B11; . . . ; H1, H3, . . . , H11) or the even-numbered wells (i.e., A2, A4, . . . , A12; B2, B4, . . . , B12; . . . ; H2, H4, . . . , H12) of a 96-well plate.

Accordingly, compounds synthesized in the first of a pair of 48-vessel reaction blocks will be transferred to the odd-numbered wells of a single microtiter plate, while compounds synthesized in the second of this pair of blocks will be transferred to the even-numbered wells, thus filling all 96 wells designated A1 through H12 in a single plate. To effect the vertical realignment of reaction block and microtiter plate in between transfers from two paired reaction blocks, either one of the reaction blocks or the underlying microtiter plate must be displaced relative to the other by a horizontal distance approximately equal to the center-to-center spacing of adjacent columns in a standard 96-well plate (about 9 mm).

Displacement of one of the reaction blocks can be accomplished, for example, by using a second transfer box cover plate wherein the various through-holes, cut-outs, and slots are slightly displaced relative to the first transfer box cover plate—or a single cover plate may have provisions for accomodating reaction blocks in either "left" or "right" positions, with odd-numbered columns of the microtiter plate being filled in the former case and even-numbered columns being filled in the latter. In yet another embodiment, the position of the microtiter plate within the transfer box cavity 888 will be shifted by an amount corresponding to the center-to-center well spacing. In this instance, a single transfer box cover plate accomodates reaction blocks in but a single fixed location, but the transfer box base may be fitted with stops or equivalent means to hold the microtiter plate in either of two positions—a "right" position where odd-numbered wells will receive cleaved compounds, and a "left" position where even-numbered wells will be filled.

A disadvantage of the above-described alternatives wherein compounds are transferred into alternating columns of a microtiter plate is that this format can be confusing to combinatorial chemists and database managers who must often associate the identity of building block reagents, chemical reactions, and/or the synthesized products on the basis of nothing more than their location in reaction blocks or microtiter plates. Indeed, the process of preparing compound libraries by parallel synthesis is sometimes referred to as "spatially addressable synthesis", and library members are identified by reaction vessel identifier and/or microtiter plate number and well identifier for purposes of tracking a compound's synthetic history and biological assay data. Accordingly, it is important that the "reformatting" of library compounds (i.e., the mapping and transfer of compounds from individual reaction vessels into individual wells in the microtiter plates used to store and assay them) be done in a manner that is as straightforward, intuitive, and error-proof as possible.

Figure 15A:
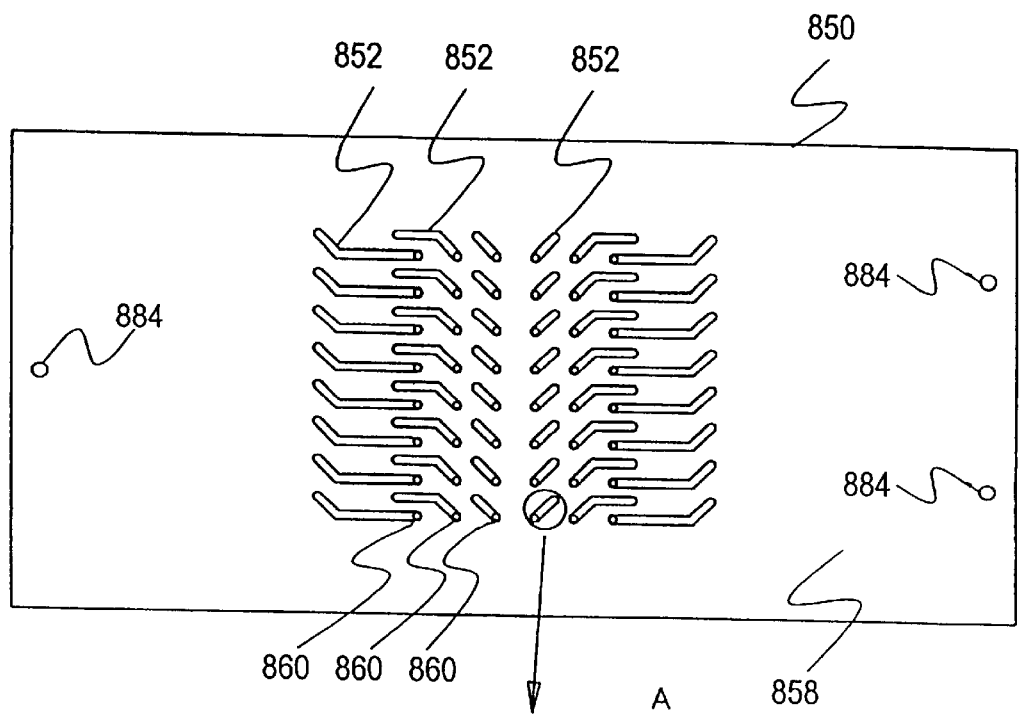
FIGS. 15A, 15B, and 15C illustrate a preferred transfer box reformatting plate. In particular.
Figure 15B:
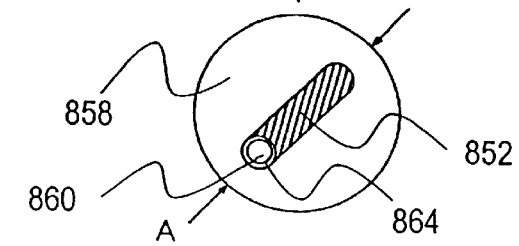
Figure 15C:
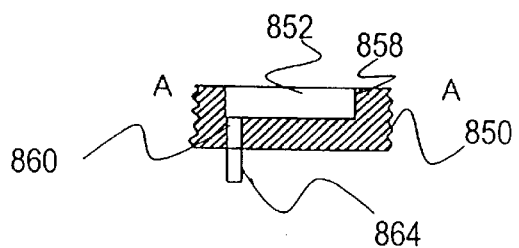

This objective is accomplished in a preferred embodiment of the present invention by transferring compounds synthesized in a reaction block into adjacent (rather than alternating) columns of the microtiter plate that receives them. In this embodiment, a plurality of director channels is provided in a suitably machined reformatting plate. The purpose of these director channels is to effect a horizontal displacement or translation of solutions of cleaved compounds after they emerge from the reaction vessel drain tubes. FIGS. 14 and 15A illustrate a particularly preferred embodiment. Here, the horizontal displacement of cleaved compound solutions is accomplished with the aid of transfer box reformatting plate 850, which has director channels 852 milled into the top surface 858 of the plate. Reformatting plate 850 is provided with a plurality of locator pins 856 that fit within transfer box base locator pin holes 884 to position the reformatting plate relative to the transfer box base. Similarly, locator pins 824 in transfer box cover plate 820 fit within transfer box reformatting plate locator pin holes 854. FIG. 15B (a magnified top view of a single director channel 852) and FIG. 15C (a cross-sectional side view of the director channel cut along vertical plane "A"—"A" in FIG. 15B) illustrate additional design details of a preferred channel. Suitable channel sizes are about 0.25 cm wide by about 0.5 cm deep.

Beneath the cover plate 820 and on top of the reformatting plate 850 is a fluid sealing gasket (not seen). This sealing gasket has plurality of holes punched through it in a pattern that precisely matches the pattern of through-holes 810. When the transfer box is assembled, the cover plate director tubes (not shown) will extend through the sealing gasket into the fluid redirector channels 852 on the top surface of the reformatting plate 850. The gasket and the fluid redirector channels therefor form a closed fluid transfer means which avoids any cross-contamination during transfer.

In operations where reformatting plate 850 is employed in the transfer of cleaved compounds, a solution containing the compound (i) emerges from reaction vessel drain tube 440, (ii) passes through its corresponding through-hole 810 in transfer box cover plate 820, and finally (iii) enters the end of reformatting plate director channel 852 that is located opposite the end of the channel where reformatting plate director channel through-hole 860 is located. Up to this point, no horizontal displacement of the solution of cleaved compound has yet taken place. However, at this point the solution flows horizontally along the length of director channel 852, ultimately to drop through transfer box reformatting plate drain hole 860. In a preferred embodiment, the drain hole 860 is fitted with reformatting plate director tube 864. Finally, solution emerging from director tube 864 falls vertically into the underlying well of multi-well microtiter plate 890.

The effect of director channels 852 provided in reformatting plate 850 is to compress laterally "columns" of cleaved compounds before being transferred into their receiving locations. As a result, solution emerges from director tubes 864 in the underside of reformatting plate 850 with a spacing between columns that corresponds to the column-to-column spacing of a standard 96-well microtiter plate—as opposed to the larger column-to-column spacing characteristic, say, of a 48-vessel reaction block.

Figure 16A:
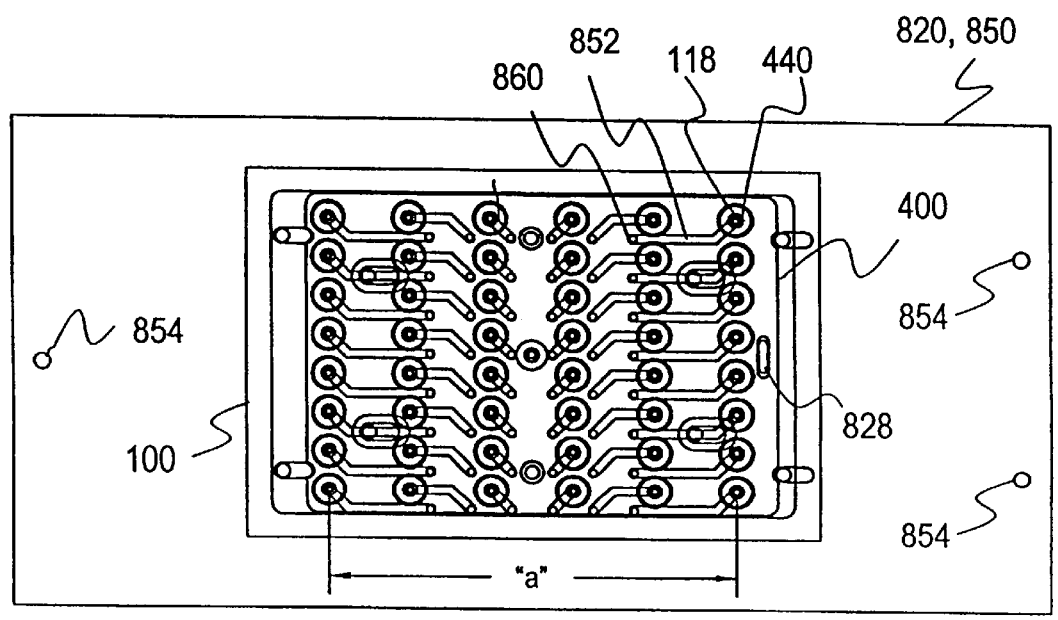
FIGS. 16A and 16B are top views of an overlay of the outline of a reaction block, a seal plate, a transfer box cover plate, and a reformatting plate with director channels, illustrating "compression" of cleaved compounds for delivery into the wells of a microtiter plate.
Figure 16B:
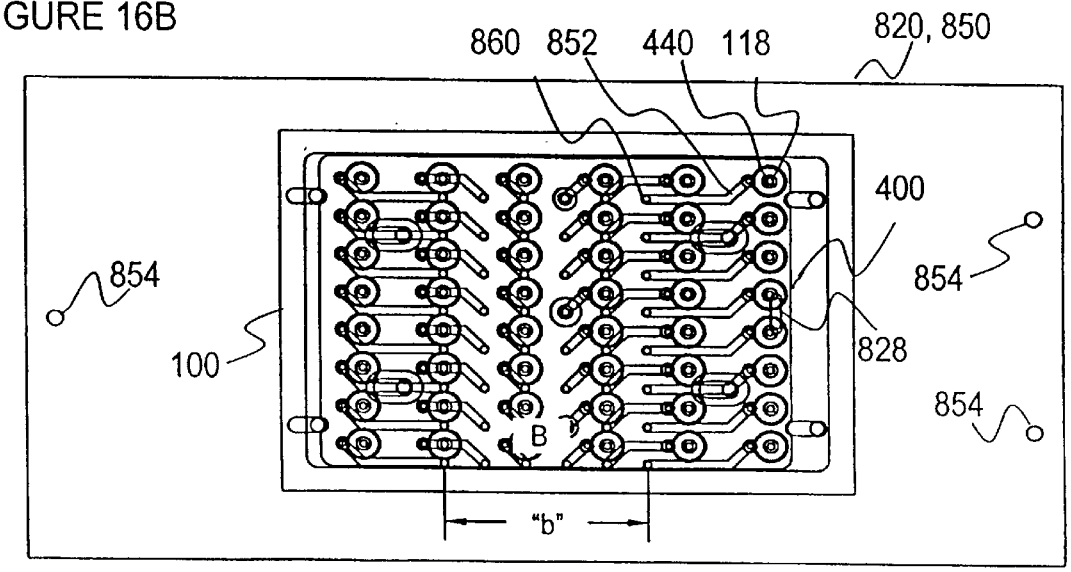

This compression may be better understood with the aid of FIGS. 16A and 16B, which show an overlay or superimposed top views of the outline of reaction block 100, seal plate 400, transfer box cover plate 820, and reformatting plate 850 with director channels 852. (Certain features of reaction block 100 and transfer box assembly 800 have been omitted from FIGS. 16A and 16B for the sake of clarity.) The effect of column compression is to take compounds produced in reaction vessels with a maximum column center-to-center spacing corresponding to distance "a" as shown in FIG. 16A and to deliver them to a series of wells with maximum column center-to-center spacing of distance "b" as shown in FIG. 16B.

FIG. 16A further illustrates the spatial relationships that exist between reaction block 100, seal plate 400, and transfer box cover plate 820 when the reaction block is slid to its left-most, "vessel-open" position. FIG. 16B illustrates the spatial relationships that exist between the reaction block, seal plate, and transfer box cover plate when the reaction block is slid to its right-most, "vessel-closed" position. When the reaction block and seal plate are in the "vessel-open" relationship of FIG. 16A, it will be noted that reaction vessel drain holes 118 are positioned directly above (i.e., are in vertical alignment with) reaction vessel drain tubes 440 and the ends of reformatting plate director channels 852 opposite the channel ends where reformatting plate drain holes 860 and director tubes 864 are located. In this configuration the apparatus enables transfer of cleaved compounds. In contrast, when the reaction block and seal plate are in the "vessel-closed" relationship of FIG. 16B, reaction vessel drain holes 118 are out of alignment with reaction vessel drain tubes 440 in seal plate 400, preventing drainage of the reaction vessels and transfer of the compounds.

Figure 17A:
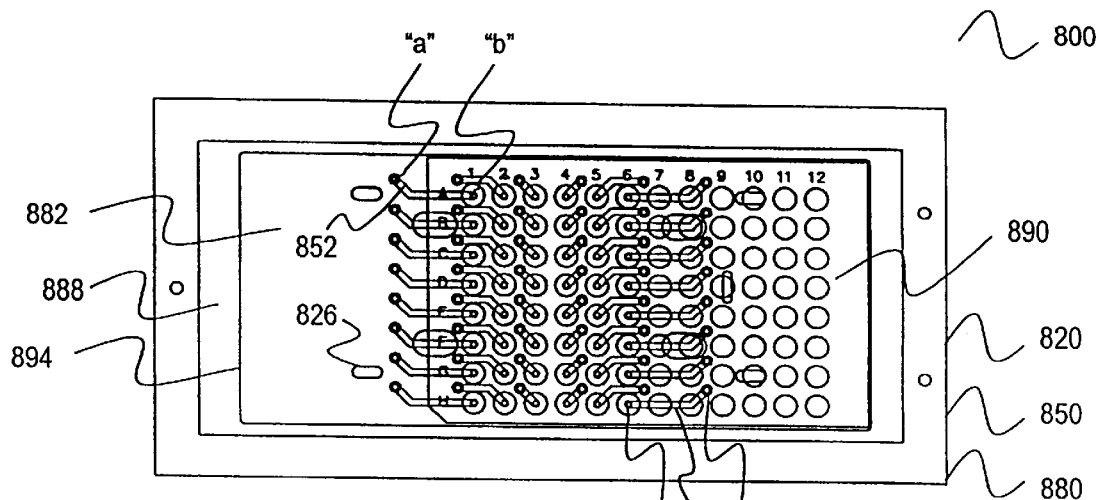
FIGS. 17A and 17B are top views of an overlay of a particularly preferred transfer box cover plate, a reformatting plate, and a transfer box base containing a microtiter plate within the transfer box cavity.

Accordingly, in this particularly preferred embodiment of the invention, the two eight-by-six arrays of compounds (or mixtures thereof) produced in each of a pair of 48-vessel reaction blocks. are compressed and transferred into adjacent halves of a single microtiter plate—rather than being interleaved, say, in alternating columns in the potentially confusing and cumbersome manner described earlier. That is, compounds synthesized in and cleaved from the first of a pair of two 48-vessel reaction blocks are transferred to wells in the first six columns of a 96-well microtiter plate— that is, into wells numbered A1, A2, . . . , A6; B1, B2, . . . , B6; . . . ; and H1, H2, . . . , H6. FIG. 17A shows an overlay (top view) of transfer box cover plate 820, reformatting plate 850, and transfer box base 880 containing microtiter plate 890 within transfer box cavity 888. It will be noted that FIG. 17A shows microtiter plate 890 located in its "right-most" position within the transfer box cavity so that the microtiter plate will be positioned to received cleaved compounds into its first six columns—that is, into wells numbered A1, A2, . . . , A6; B1, B2, . . . , B6; . . . ; and H1, H2, . . . , H6. For instance, fluid containing the cleaved compound prepared in reaction vessel A1 located at the "top-left" position of this first of a pair of 48-vessel reaction blocks will enter "top-left" director channel 852 at point "a" as shown in FIG. 17A, subsequently travelling along the channel to drop through the reformatting plate at point "b" into underlying well A1 of microtiter plate 890. At the same time, fluid containing the cleaved compound prepared in reaction vessel H6 located at the "bottom-right" position of this first of a pair of 48-vessel reaction blocks will enter "bottom-right" director channel 852 at point "c" as shown in FIG. 17A, subsequently travelling along the channel to drop through the reformatting plate at point "d" into underlying well H6 of microtiter plate 890.

Figure 17B:
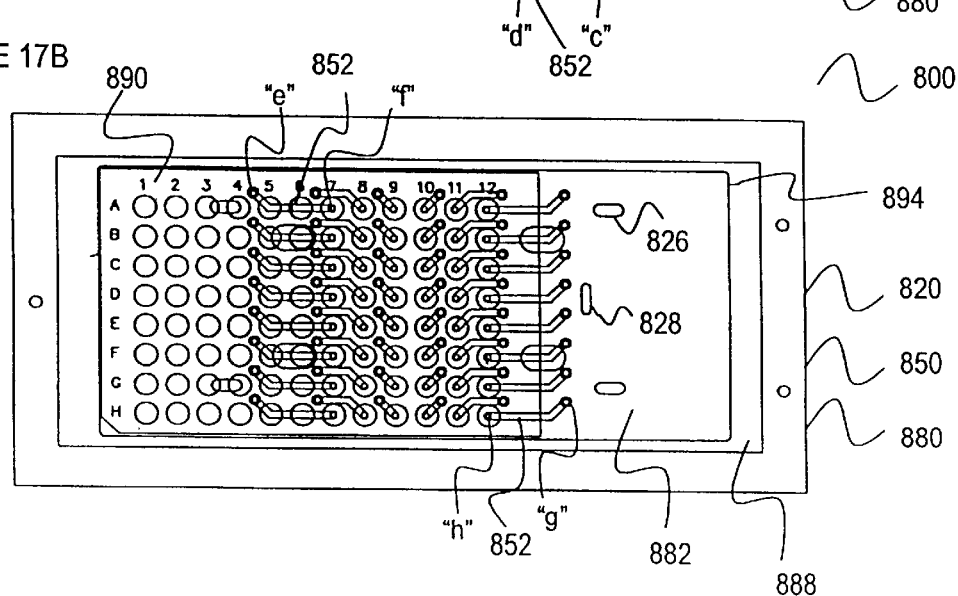

A similar operation is performed with compounds synthesized in and cleaved from the second of a pair of two 48-vessel reaction blocks, except that in this case cleaved compounds are transferred to wells in the last six columns of the 96-well microtiter plate that is, into wells numbered A7, AB, . . . , A12; B7, B8, . . . , B12; . . . ; and H7, H8, . . . , H12. FIG. 17B shows an overlay (top view) of transfer box cover plate 820, reformatting plate 850, and transfer box base 880 containing microtiter plate 890 within transfer box cavity 888. In this instance, however, FIG. 17B shows microtiter plate 890 located in its "left-most" position within the transfer box cavity so that the microtiter plate will be positioned to received cleaved compounds into its last six columns—that is, into wells numbered A7, A8, . . . , A12; B7, B8, . . . , B12; . . . ; and H7, H8, . . . , H12. For instance, fluid containing the cleaved compound prepared in reaction vessel A7 located at the "top-left" position of this second of a pair of 48-vessel reaction blocks will enter "top-left" director channel 852 at point "e" as shown in FIG. 17B, subsequently travelling along the channel to drop through the reformatting plate at point "f" into underlying well A7 of microtiter plate 890. At the same time, fluid containing the cleaved compound prepared in reaction vessel H12 located at the "bottom-right" position of second of a pair of 48-vessel reaction blocks will enter "bottom-right" director channel 852 at point "g" as shown in FIG. 17B, subsequently travelling along the channel to drop through the reformatting plate at point "h" into underlying well H12 of microtiter plate 890.

Thus, the position of microtiter plate 890 in transfer box base cavity 888 is shifted horizontally and to the left by a distance corresponding to six times the center-to-center spacing between wells in adjacent columns of the microtiter plate. This microtiter plate realignment can be accomplished, for example, simply by pushing the microtiter plate from one end to the other end of transfer box base cavity 888, or the microtiter plate may be pushed back and forth from one stop 894 (e.g., a "left" stop) to a second stop 894 (e.g., a "right" stop). As shown in FIGS. 17A and 17B, stops 894 may consist of the lip or edge of recessed area 882 that is milled into the floor of transfer box base 880. The microtiter plate may be moved between stops manually, or various mechanical means (e.g., pusher rods) may be employed for this purpose.

These operations ultimately result in all 96 wells of the microtiter plate being filled with the compounds (or compound mixtures) produced in a pair of 48-chamber reaction vessels. The compound transfer process of the current invention is very straightforward, intuitive, and readily documented, thus substantially reducing the potential for confusion and error in this final step of combinatorial library preparation.

Solid phase parallel synthesis has an advantage over solution-phase chemistry in its easy separation of soluble reagents by simple filtration. Ready removal of solution-phase reagents from solid-phase products permits excess reagents to be used for driving reactions towards complete conversion. On the other hand, many limitations exist in the range of chemistries that can be performed on a solid support—limitations that are particularly pronounced in the synthesis of small heterocyclic, drug-like molecules. If equipment existed for separating soluble reactants and other reaction auxiliaries from soluble reaction products, more powerful solution-phase chemistries could be applied to the synthesis of a wider range of potential drug-like molecules. However, existing automation devices and equipment have been designed to address parallel, high-speed reagent dispensing, and not the purifications required of solution-phase mixtures of reagents and products.

The combination of the multi-valve design of the present reaction block due to the sliding seal plate and the fluid reformatting and redirection capabilities of the "transfer" box permit separation and purification in the context of solution-phase parallel synthesis. The ability of the reaction block to undergo rapid and uniform heating and cooling of the reaction block facilitates parallel liquid-liquid extraction by a freeze-thaw phase separation technique. Equally important to the use of the system in solution-phase synthesis is its ability to direct fluids emerging from the reaction vessels into receivers of various geometries, layouts, and physical sizes. This reformatting/redirection capability has been described above primarily for the cleavage of products from a solid phase and then transfer into variously sized microtiter plates and the like. However, the same "transfer" box (referred to in the context of solution-phase purification and Example 2 below as a "purification" box) also manages fluids being manipulated during solution-phase separation and purification operations. This is effected in a straightforward manner by modifying the dimensions, layout, and pattern of the fluid redirection channels in the box cover plate to direct solutions to receiver vessels (or arrays thereof) appropriate to various work-up procedures and by adjusting the size of the box to accommodate receivers of various physical dimensions and layouts (including additional reaction blocks to be used in subsequent synthetic steps).

Any number of mechanical design variations will be apparent to those of ordinary skill in the art, all of which are encompassed by the method and apparatus of the present invention as described herein and claimed below.

EXAMPLE 1

Solid Phase Synthesis

This example illustrates use of the present invention in high-throughput organic synthesis and combinatorial chemistry. A solid-phase parallel synthesis of a library of 96 discrete chemical compounds is described. Synthetic operations are described for one 48-vessel reaction block—i.e., the first of a pair of blocks wherein a total of 96 compounds are synthesized. Similar operations would be carried out in parallel with the second of this pair of reaction blocks. Procedures for the two blocks differ only in the last step of compound cleavage and transfer where compounds prepared in the first block are transferred into the first six columns of a 96-well microtiter plate and compounds prepared in the second block are transferred into the last six columns of the microtiter plate.

Reactant addition. Prior to adding materials, the reaction block will first be placed in its "vessel-closed" configuration by sliding the seal plate to its appropriate stop. Next, solid-phase support resin, reagent solutions, and/or other reaction auxiliaries (e.g., catalysts) are dispensed into the reaction vessels manually or via automated means. When noxious reactants and/or solvents are used, a perforated cover plate is employed, and the reactants are injected into the vessels of a septum-sealed reaction block apparatus with the aid of the perforated cover plate. The gas/vapor space within the reaction block apparatus may be purged with an inert gas if desired during the reagent addition process, to exclude atmospheric constituents, e.g. oxygen or water vapor, that might interfere with the reaction.

Reaction. Certain reactions—especially those involving only relatively low-volatility compounds and solvents at ambient temperature—are conducted with the reaction block open to the atmosphere. Other reactions will require that the block be tightly sealed—top and/or bottom—with a cover plate and baseplate to ensure retention of the contents of the reaction vessels. If heating and/or cooling is needed during a reaction step, an optional heat/cool cover plate may be installed instead of the solid or perforated cover plates. Agitation of the reaction block is provided by placing it atop an orbital shaker. Purging is accomplished by feeding an inert gas like nitrogen or argon to the reaction block while its contents are being incubated.

Resin washing. After the reaction has proceeded for a suitable period of time, the reaction block is mounted atop a wash plate apparatus for resin washing operations. Once in place, a partial vacuum is applied to the underside of the reaction block and the sliding seal plate moved to its "vessel-open" position. These actions cause the liquid contents of the reaction vessels to drain to waste. The vacuum pump or line is then shut off following which additional wash solvent is added to each of the reaction vessels. The reaction block is optionally agitated for some period of time. Then, vacuum is applied once more through the wash plate, and wash solvent is removed to waste by aspiration. The operations of wash solvent dispensing, incubation/agitation, and aspiration are applied repeatedly—with different wash solvents employed in subsequent cycles—to improve the efficiency of resin washing. Once resin washing is complete, the sliding seal plate is moved to its "vessel-closed" position.

Additional reaction cycles. The above-described steps of reagent addition, reaction, and resin washing are repeated (albeit with different reagents as needed) to conduct additional reaction steps in the combinatorial synthesis. After the last chemical reaction, the solid-phase support resin to which the desired products are attached will be washed a final time, excess wash solvent will be removed by aspiration, and the sliding seal plate will be moved to its "vessel-closed" position.

Compound cleavage and transfer. Once the chemical syntheses are completed, covalently bound library compounds are cleaved from their solid supports by adding a cleavage reagent (e.g., trifluoroacetic acid) to the reaction vessels. The reaction block is sealed and/or agitated during this process. Next, a microtiter plate is installed in its right-most position within the cavity of the transfer box so that cleaved compounds are transferred to the wells of its first six columns. Cover and reformatting plates are then put in place atop the transfer box, and the reaction block is then positioned atop the cover plate.

To initiate compound transfer, a vacuum is applied to the transfer box base, and the reaction block is then slid across the top surface of the transfer box cover plate, placing the reaction block in its "vessel-open" configuration. This causes aspiration of solutions from the reaction vessels and the transfer of cleaved compounds to the appropriate wells of the underlying microtiter plate.

Similar operations are conducted in parallel with a second 48-vessel reaction block. Prior to compound cleavage and transfer from this second block, the aforesaid microtiter plate (half of its wells containing compounds from the first block) will be moved within the transfer box into its left-most position, thus preparing it to accept compounds in the wells of its last six columns. With this exception of microtiter plate placement, compound transfer from this second of the pair of reaction blocks proceeds just as described above for the first of the pair.

In this manner, 96 discrete compounds (or compound mixtures) are synthesized and stored using the method and apparatus of the present invention.

EXAMPLE 2

Solution-Phase Synthesis

Use of the multi-valve design of the present reaction block and the fluid reformatting and redirection of the "transfer/purification" box to perform separations and purifications in a solution-phase parallel synthesis is detailed below.

Reactant addition. The initial reactant additions to the vessels is the same as in the solid-phase system of Example 1. Prior to the addition of materials to the reaction vessels, the reaction block is first placed in a "vessels-closed" configuration by sliding the seal plate to its appropriate stop. Next, reagent solutions and/or other reaction auxiliaries are dispensed into the reaction vessels manually or via automated means. Where reactants and/or solvents are noxious, a perforated cover plate is employed for containment, with the reactants being injected via needles or cannula into the vessels of the septum-sealed reaction block apparatus. The gas or vapor space within the reaction block apparatus may also be purged with an inert gas during the reagent addition process to exclude atmospheric constituents such as oxygen or water vapor that might subsequently interfere with the reaction.

Reaction. Certain reactions—especially those involving only relatively low-volatility compounds and solvents at ambient temperature—may be conducted with the reaction block open to the atmosphere. Other reactions will require that the block be tightly sealed—top and/or bottom—with a cover plate and baseplate to ensure retention of the contents of the reaction vessels. If it is desired to heat and/or cool the apparatus during the reaction step, an optional heat/cool cover plate may be installed instead of the solid or perforated cover plates mentioned above. Agitation of the reaction block may be provided by placing it atop an orbital shaker. Purging may be accomplished by feeding an inert gas like nitrogen or argon to the reaction block while its contents are incubated.

Suitable alternative reaction workup procedures using the reaction block system of the present invention are provided.

1. Liquid-liquid extraction. Traditionally, liquid-liquid extraction is utilized during reaction workup to remove water-soluble reagents and/or byproducts from the organic phase that typically contains the desired reaction product or intermediate. At the lab-bench scale, extractions are most often performed in separatory funnels; following contact of the two immiscible phases, the typically buffered aqueous layer and organic layer are then separated from one another by drawing off the denser phase (usually, but not always, the aqueous phase) or by decanting the lighter phase. The same approach cannot be applied to multiple samples prepared in the context of parallel synthesis, however, due to the difficulty of simultaneously and cleanly separating one liquid layer from the other in a parallel manner using simple cut-off switches.

After reaction has proceeded for a suitable period of time, the reaction solution is optionally concentrated to dryness by a stream of nitrogen, following which the recovered material is then redissolved in a solvent more appropriate for subsequent purification steps. An aqueous buffer solution is then dispensed into each reaction vessel manually or via automated means. The reaction block can then be agitated for some period of time, after which it is immersed in a low-temperature dry-ice/solvent bath or the like cooled to freeze at least part of its fluid contents. After the aqueous phase is frozen, a second, empty reaction block (a "receiving" block) is placed in a purification box to collect the organic phases contained in the individual vessels of the first reaction block. The first block (the "product" block) containing both the organic phase (as a liquid) and the aqueous phase (as a frozen solid) is then placed atop the purification box. When the frozen aqueous phase in the product block starts melting, a gentle vacuum is applied to the purification box, and the product block is slid across the top surface of the purification box cover plate to move the sliding seal plate to its "vessels-open" position. This causes the organic phase to be pulled past the frozen aqueous-phase "plug" and filtered through the reaction vessel bottom frits into the receiving block inside of the purification box. The operations of buffer solution dispensing, agitation and freeze-thaw filtration can be applied repeatedly, with different aqueous buffer solutions employed in subsequent cycles. Once organic-phase washing cycles are completed, the organic layer can be dried over $Na_2SO_4$ or $MgSO_4$ and filtered, following which the solvent can be removed by evaporation into a stream of nitrogen.

2. Liquid-liquid phase separation. The reaction block and system can also be used in the context of extractions where the subsequent liquid-liquid (e.g., aqueous/organic) phase separation is conducted by more conventional means. In particular, manual or robotically controlled needles or cannula can be used to withdraw or "sip" most of one of the phases from individual reaction vessels—an operation that is facilitated by the use of needles or devices equipped with interface-detection means.

3. Scavenger or ion-exchange resins. Scavenger resin and ion-exchange resins are widely used in solution-phase parallel synthesis to remove excess soluble reagents and/or other impurities (and, in certain cases, to recover reaction products). The simplicity of using polymer-bound adsorbents or reagents to ionically or covalently interact with soluble reagents and thus permit their separation by liquid/solid filtration makes these "resin-capture" methods extremely attractive to chemists.

"Resin capture" with the system is illustrated for a resin having an affinity for excess reagents and/or other impurities. After the reaction has proceeded for a suitable period of time, scavenger or ion-exchange resin dispensed in an appropriate solvent is added to each reaction vessel, and the resulting slurry is then agitated for an appropriate length of time. An empty reaction block (the "receiving" block) which is to used in the next step of a reaction scheme is then placed in a purification box. The reaction block that contains the slurry of reaction solution and scavenger or ion-exchange resin (the "product" block) is placed atop the purification box. To initiate filtration, a gentle vacuum is applied to the purification box, and the product block is slid across the top surface of the purification box cover plate to move the sliding seal plate to its "vessels-open" position. This causes filtration of reaction products through the bottom frits of the product block into the receiving block (or array of glass vials or deep-well microtiter plate) within the purification box. The resin in the product block is then washed with organic solvent to improve product recovery. Such resin-capture/filtration/washing cycles can be performed repeatedly—with different scavenger resins employed in subsequent cycles—to remove unreacted reagents and/or other impurities from the desired synthetic product.

Using multiple reaction blocks with frits at the bottom of each reaction vessel—both to receive filtered fluids and to perform resin capture—greatly facilitates these repetitive operations. Substantially similar cyclic operations are conducted where the resin has an affinity for the desired product—the main difference being that the captured product must eventually be separated (e.g., by desorption or elution) from the resin.

4. Solid-phase extraction (SPE). SPE has historically been used in laboratories for sample concentration and preparation prior to instrumental analyses. However, the burst of activity in combinatorial synthesis in recent years has rapidly expanded the application of SPE to the areas of organic synthesis and medicinal chemistry. The main challenge in using SPE in parallel purification is the relatively low capacity of the solid sorbent frequently requires use of a large amount of purification media, resulting in an incompatibility between the footprints of a small reaction block and an array of large SPE purification cartridges. This difficulty is ameliorated by the fluid reformatting/redirection capability of the present invention.

This utility is illustrated here for the case of a product which is to be recovered by sorption onto an appropriate SPE material. After reaction has proceeded for a suitable period of time, the reaction products are optionally evaporated to dryness with a stream of nitrogen and then redissolved into a solvent that is more appropriate for subsequent purification steps. An array of preconditioned SPE reservoirs or an SPE "plate" is then placed into a purification box. The reaction block is then placed atop the purification box. To initiate the transfer of reaction products from the reaction block into the SPE reservoirs or plate, a gentle vacuum is applied to the purification box, and the reaction block is slid across the top surface of the purification box cover plate to move the sliding seal plate to its "vessels-open" position. This causes reaction products to pass through the fluid redirection channels in the cover plate and into either the SPE reservoirs or the wells of the SPE plate located inside of the purification box. The SPE reservoirs or plate can then be rinsed (to remove adhering liquid containing contaminants), and the reaction products can then be eluted either into an empty reaction block (for the next reaction step) or into an array of glass vials or a deep-well microtiter plate for final product archiving.

Although the present invention has been described in terms of a preferred embodiment, those of ordinary skill in the art will recognize that many design variations are possible that will still lie within the scope of the present invention. In particular, the scope of the present invention is not limited to the embodiments depicted and described herein—but rather is defined by the appended claims.

What is claimed is:

1. An apparatus for use in synthesizing a library of organic compounds comprising:
   (a) a reaction block assembly comprising:
      (i) a reaction block having multiple individual reaction vessels, each of said vessels having an open top and a bottom surface with a drain hole located therein; and
      (ii) a sealing means for simultaneously sealing the drain holes of each of the reaction vessels in the reaction block, said sealing means having a plurality of through-holes spatially corresponding to the drain holes of the reaction vessels and movable into and out of fluid communication with said drain holes;
   (b) a washing plate assembly comprising a means for attaching the reaction block; a recessed wash plate cavity in fluid communication with a fluid exit port; and a means for simultaneously controlling the drainage of all of the reaction vessels;
   (c) a transfer assembly comprising a transfer box having an internal cavity sized to fit a receiving container, a transfer cover plate shaped to mate with the reaction block assembly, and a means for locating the transfer assembly cover plate on the transfer box;
   (d) a top cover plate which seals the tops of the reaction vessels as a group and forms a closed top compartment above the tops of the reaction vessels;
   (e) a base plate which encloses the bottom of the reaction block and the sealing means to form a closed bottom compartment;
   (f) a pressure equalization through-hole extending through the reaction block from the top compartment to the bottom compartment; and
   (g) means for opening and closing the pressure equalization through-hole comprising the sealing means which includes a through-hole spatially corresponding to the pressure equalization through-hole;
   wherein the pressure equalization through-hole opens when the sealing means closes the reaction vessel drain holes.

2. The apparatus of claim 1 wherein the pressure equalization through-hole closes when the sealing means opens the reaction vessel drain holes.

3. The apparatus of claim 1, wherein reaction vessel drain tubes are fixed within the through-holes of the sealing means.

4. The apparatus of claim 1, wherein the reaction block is formed from a single piece of material.

5. The apparatus of claim 1, wherein the reaction block is assembled from a reaction block top piece and a reaction block bottom piece.

6. The apparatus of claim 5, wherein the reaction block top piece and reaction block bottom piece are joined together by placing a polymeric film between the pieces and followed by heating under compression.

7. The apparatus of claim 1, wherein the sealing means is a sliding seal plate.

8. The apparatus of claim 7, wherein the sliding seal plate contains through slots which limit the sliding motion to a single axis.

9. The apparatus of claim 7, wherein the sliding seal plate is held in close proximity to and coplanar with the bottom of the reaction block by a spring means.

10. The apparatus of claim 9, wherein the spring means comprises a threaded screw extending through a spring which allows adjustment of compression of the spring.

11. The apparatus of claim 1, wherein the top cover plate includes a plurality of perforations spatially substantially corresponding to the tops of the reaction vessels.

12. The apparatus of claim 11, wherein a solvent-resistant elastomeric rubber septum is placed atop the reaction vessels and below the top perforated cover plate.

13. The apparatus of claim 1, wherein the top cover plate is an assembly comprising a top cover plate having a plurality of perforations spatially substantially corresponding to the tops of the reaction vessels, a solvent-resistant elastomeric rubber septum, and a bottom cover plate having a plurality of perforations spatially substantially corresponding to both the tops of the reaction vessels and to the perforations of the top cover plate.

14. The apparatus of claim 1, further including a reaction block heat/cool plate assembly comprising a cover plate box which mates with the top of the reaction block and which has an interior passage through which a heat-transfer liquid may pass.

15. The apparatus of claim 1, wherein the wash plate cavity is sloped toward the fluid exit port.

16. The apparatus of claim 1, wherein the transfer assembly cover plate includes a plurality of holes spatially corresponding to the drain holes of the reaction vessels of the reaction block.

17. The apparatus of claim 16, wherein drain tubes are fixed within the through-holes of the transfer assembly cover plate.

18. The apparatus of claim 17, wherein the transfer assembly cover plate drain tubes lead directly into a receiving container.

19. The apparatus of claim 18, wherein the receiving container is selected from the group consisting of a multi-well microtiter plate, a second reaction block assembly, an array of glass vials, and an array of sorbent media.

20. The apparatus of claim 17, wherein the transfer assembly cover plate drain tubes lead to a fluid redirecting means which horizontally transfers fluids drained from the reaction block prior to transfering the fluids into a receiving container.

21. The apparatus of claim 20, wherein the fluid redirecting means comprises channels in a transfer plate, said channels originating directly below the transfer assembly drain tubes and terminating in holes.

22. The apparatus of claim 1, wherein porous frits are located at the bottom of each reaction vessel.

* * * * *